(12) United States Patent
Brady et al.

(10) Patent No.: US 7,132,401 B2
(45) Date of Patent: Nov. 7, 2006

(54) BETA-SECRETASE SUBSTRATES AND USES THEREOF

(75) Inventors: Stephen F. Brady, Philadelphia, PA (US); James E. Bruce, Schwenksville, PA (US); Elizabeth Chen-Dodson, Souderton, PA (US); Victor Garsky, Blue Bell, PA (US); Yueming Li, New York, NY (US); Mohinder Sardana, Lansdale, PA (US); Jules A. Shafer, Gwynedd Valley, PA (US); Xiaoting Tang, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/480,954

(22) PCT Filed: May 17, 2002

(86) PCT No.: PCT/US02/15590

§ 371 (c)(1),
(2), (4) Date: Jul. 22, 2004

(87) PCT Pub. No.: WO02/094985

PCT Pub. Date: Nov. 28, 2002

(65) Prior Publication Data

US 2005/0032190 A1   Feb. 10, 2005

(51) Int. Cl.
*A61K 38/08* (2006.01)
(52) U.S. Cl. .......................................... 514/16; 435/7.1
(58) Field of Classification Search ................... 514/16; 435/7.1
See application file for complete search history.

(56) References Cited

U.S. PATENT DOCUMENTS 6,203,979 B1   3/2001   Bandman et al.
2005/0170489 A1 *  8/2005   Anderson et al. ........... 435/226

OTHER PUBLICATIONS

Gau et al. Am. J. Pathology, Feb. 2002, vol. 160, p. 731-737.*
Brown, A. M. et al., "Evaluation of Cathepsins D and G and EC 3.4.24.15 As Candidate β-Secretase Proteases Using Peptide and Amyloid Precursor Protein Substrates", Journal of Neurochemistry, vol. 66, 6:2436-2445. 1996.
Yankner et al., "Neurotoxicity of a Fragment of the Amyloid Precursor Associated with Alzheimer's Disease", Science, 245: 417-420, 1989.
Frautschy et al., "Effects of Injected Alzheimer β-Amyloid Cores in Rat Brain", Proc. Natl. Acad. Sci. USA, 88: 8362-8366, 1991.
Kowall et al., "An *in vivo* Model for the Neurodegenerative Effects of β Amyloid and Protection by Substance P", Proc. Natl. Acad. Sci. USA, 88: 7247-7251, 1991.
Geula et al., "Aging Renders the Brain Vulnerable to Amyloid β-Protein Neurotoxicity", Nature Medicine, 4:827-831, 1998.

Selkoe, Dennis J., "Alzheimer's Disease: A Central Role for Amyloid", J. Neuropathol. Exp. Neurol., 53:438-447, 1994.
Selkoe, Dennis J., "The Cell Biology of β-Amyloid Precursor Protein and Presenilin in Alzheimer's Disease", Trends Cell Biol., 8: 447-453, 1998.
Ponte et al., "A New A4 Amyloid mRNA Contains a Domain Homologous to Serine Proteinase Inhibitors", Nature, 331: 525-527, 1988.
Tanzi et al., "Protease Inhibitor Domain Encoded by an Amyloid Protein Precursor mRNA Associated with Alzheimer's Disease", Nature, 331: 528-530; 1988.
Kitaguchi et al., "Novel Precursor of Alzheimer's Disease Amyloid Protein Shows Protease Inhibitory Activity", Nature 331: 530-532, 1988.
Kang et al., "The Precursor of Alzheimer's Disease Amyloid A4 Protein Resembles a Cell-Surface Receptor", Nature, 325: 773-776, 1987.
Kuentzel et al., "The Alzheimer β-Amyloid Protein Precursor/Protease Nexin-II is Cleaved by Secretase in a *trans*-Golgi Secretory Compartment in Human Neuroglioma Cells", Biochem. J., 295: 367-378, 1993.
Selkoe, Dennis J., "Cell Biology of the Amyloid β-Protein Precursor and the Mechanism of Alzheimer's Disease", Ann. Rev. Cell Biol, 10: 373-403, 1994.
Esch et al., "Cleavage of Amyloid β Peptide During Constitutive Processing of Its Precursor", Science, 248: 1122-1124, 1994.
Glenner et al., "Alzheimer's Disease: Initial Report of the Purification and Characterization of a Novel Cerebrovascular Amyloid Protein", Biochem. Bophys. Res. Comm., 120: 885-890, 1984.
Masters et al., "Amyloid Plaque Core Protein in Alzheimer's Disease and Down Syndrome", Proc. Natl. Acad. Sci. USA, 82: 4245-4249, 1985.
Haass et al., "Amyloid β-Peptide is Produced by Cultured Cells During Normal Metabolism", Nature, 359:322-325, 1992.
Seubert et al., "Isolation and Quantification of Soluble Alzheimer's β-Peptide From Biological Fluids", Nature, 359: 325-327, 1992.
Vassar et al., "β-Secretase Cleavage of Alzheimer's Amyloid Precursor Protein by the Transmembrane Aspartic Protease BACE", Science, 286: 735-741; 1999.
Hussain et al., "Identification of a Novel Aspartic Protease (Asp 2) as β-Secretase", Mol. Cell. Neurosci., 14: 419-427, 1999.
Yan et al., "Membrane-Anchored Aspartyl Protease with Alzheimer's Disease β-Secretase Activity", Nature, 402: 533-537, 1999.

(Continued)

*Primary Examiner*—Michael Borin
(74) *Attorney, Agent, or Firm*—Joan E. Switzer; Joanne M. Giesser

(57) ABSTRACT

The present invention provides synthetic β-secretase peptide substrates useful in various assays for measuring β-secretase activity. Antibodies that recognize the synthetic substrates and uses of the antibodies in various assays are disclosed. The herein disclosed peptide substrates are hydrolyzed at rates substantially faster than the attendant Swedish mutant APP from which the substrate sequences are derived.

5 Claims, 4 Drawing Sheets

OTHER PUBLICATIONS

Sinha et al., "Purification and Cloning of Amyloid Precursor Protein β-Secretase from Human Brain", Nature, 402: 537-540, 1999.

Lin et al., "Human Aspartic Protease Memapsin 2 Cleaves the β-Secretase Site of β-Amyloid Precursor Protein", Proc. Natl. Acad. Sci. USA, 97: 1456-1460, 2000.

Citron, Martin; "Secretases as Targets for the Treatment of Alzheimer's Disease", Molecular Medicine Today, 6: 392-397, 2000.

Hardy, John; "Framing β-Amyloid", Nature Genet., 1: 233-234, 1992.

Yang et al., "Electrochemiluminescence: A New Diagnostic and Research Tool", Bio Technology, 12: 193-194; 1994.

Khorkova et al., "Modulation of Amyloid Precursor Protein Processing by Compounds with Various Mechanisms of Action: Detection by Liquid Phase Electrochemiluminescent System", Journal of Neuroscience Methods, 82: 159-166, 1998.

* cited by examiner

Combinatorial peptide libraries based on APP
Sequence flanking the BACE scissile bond:

E - V - N - L - D - A - E - F  (APP, Swedish, SEQ ID NO: 257)

| X  | P3 | P2 | P1 | P1' | P2' | P3' | P4' |
|----|----|----|----|-----|-----|-----|-----|
| P4 | X  | P2 | P1 | P1' | P2' | P3' | P4' |
| P4 | P3 | X  | P1 | P1' | P2' | P3' | P4' |
| P4 | P3 | P2 | X  | P1' | P2' | P3' | P4' |
| P4 | P3 | P2 | P1 | X   | P2' | P3' | P4' |
| P4 | P3 | P2 | P1 | P1' | X   | P3' | P4' |
| P4 | P3 | P2 | P1 | P1' | P2' | X   | P4' |
| P4 | P3 | P2 | P1 | P1' | P2' | P3' | X   |

FIG.1

SEQUENCE LISTING

<160> NUMBER OF SEQ ID NOS: 264

<210> SEQ ID NO 1
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 1

Glu Ile Tyr Leu Glu Val Ile Trp
1               5

<210> SEQ ID NO 2

```
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 2

Glu Ile Tyr Phe Glu Val Val Trp
 1               5

<210> SEQ ID NO 3
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 3

Asp Ile Tyr Leu Glu Val Ile Trp
 1               5

<210> SEQ ID NO 4
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 4

Asp Ile Tyr Phe Glu Val Val Trp
 1               5

<210> SEQ ID NO 5
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 5

Glu Val Tyr Leu Glu Val Ile Trp
 1               5

<210> SEQ ID NO 6
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 6

Glu Val Tyr Phe Glu Val Val Trp
 1               5

<210> SEQ ID NO 7
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 7

Asp Val Tyr Leu Glu Val Ile Trp
 1               5

<210> SEQ ID NO 8
<211> LENGTH: 8
```

```
<212> TYPE: PRT
<213> ORGANISM: Artificial Sequence
<220> FEATURE:
<223> OTHER INFORMATION: Beta-Secretase Cleavage Site

<400> SEQUENCE: 8

Asp Val Phe Phe Glu Ala Ile Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 9

Glu Ile Phe Leu Glu Val Ile Trp
1               5

<210> SEQ ID NO 10
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 10

Glu Ile Tyr Leu Ala Ala Ile Pro
1               5

<210> SEQ ID NO 11
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 11

Asp Ile Phe Leu Glu Val Ile Trp
1               5

<210> SEQ ID NO 12
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 12

Asp Ile Tyr Leu Ala Ala Ile Pro
1               5

<210> SEQ ID NO 13
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 13

Glu Val Phe Leu Glu Val Ile Trp
1               5

<210> SEQ ID NO 14
<211> LENGTH: 8
<212> TYPE: PRT
```

```
<213> ORGANISM: Artificial Sequence
<220> FEATURE:
<223> OTHER INFORMATION: Beta-Secretase Cleavage Site

<400> SEQUENCE: 14

Glu Val Tyr Leu Ala Ala Ile Pro
 1               5

<210> SEQ ID NO 15
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 15

Asp Val Phe Leu Glu Val Ile Trp
 1               5

<210> SEQ ID NO 16
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 16

Asp Val Tyr Leu Ala Ala Ile Pro
 1               5

<210> SEQ ID NO 17
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 17

Glu Ile Tyr Phe Glu Val Ile Trp
 1               5

<210> SEQ ID NO 18
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 18

Glu Ile Phe Leu Ala Ala Ile Pro
 1               5

<210> SEQ ID NO 19
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 19

Asp Ile Tyr Phe Glu Val Ile Trp
 1               5

<210> SEQ ID NO 20
<211> LENGTH: 8
<212> TYPE: PRT
<213> ORGANISM: Artificial Sequence
```

```
<220> FEATURE:
<223> OTHER INFORMATION: Beta-Secretase Cleavage Site

<400> SEQUENCE: 20

Asp Ile Phe Leu Ala Ala Ile Pro
 1               5

<210> SEQ ID NO 21
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 21

Glu Val Tyr Phe Glu Val Ile Trp
 1               5

<210> SEQ ID NO 22
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 22

Glu Val Phe Leu Ala Ala Ile Pro
 1               5

<210> SEQ ID NO 23
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 23

Asp Val Tyr Phe Glu Val Ile Trp
 1               5

<210> SEQ ID NO 24
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 24

Asp Val Phe Leu Ala Ala Ile Pro
 1               5

<210> SEQ ID NO 25
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 25

Glu Ile Phe Phe Glu Val Ile Trp
 1               5

<210> SEQ ID NO 26
<211> LENGTH: 8
<212> TYPE: PRT
<213> ORGANISM: Artificial Sequence
<220> FEATURE:
```

<223> OTHER INFORMATION: Beta-Secretase Cleavage Site

<400> SEQUENCE: 26

Glu Ile Tyr Phe Ala Ala Ile Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 27

Asp Ile Phe Phe Glu Val Ile Trp
1               5

<210> SEQ ID NO 28
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 28

Asp Ile Tyr Phe Ala Ala Ile Pro
1               5

<210> SEQ ID NO 29
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 29

Glu Val Phe Phe Glu Val Ile Trp
1               5

<210> SEQ ID NO 30
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 30

Glu Val Tyr Phe Ala Ala Ile Pro
1               5

<210> SEQ ID NO 31
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 31

Asp Val Phe Phe Glu Val Ile Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Beta-Secretase Cleavage Site

```
<400> SEQUENCE: 32

Asp Val Tyr Phe Ala Ala Ile Pro
1               5

<210> SEQ ID NO 33
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 33

Glu Ile Tyr Leu Ala Val Ile Trp
1               5

<210> SEQ ID NO 34
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 34

Glu Ile Phe Phe Ala Ala Ile Pro
1               5

<210> SEQ ID NO 35
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 35

Asp Ile Tyr Leu Ala Val Ile Trp
1               5

<210> SEQ ID NO 36
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 36

Asp Ile Phe Phe Ala Ala Ile Pro
1               5

<210> SEQ ID NO 37
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 37

Glu Val Tyr Leu Ala Val Ile Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Beta-Secretase Cleavage Site
```

-continued

```
<400> SEQUENCE: 38

Glu Val Phe Phe Ala Ala Ile Pro
1               5

<210> SEQ ID NO 39
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 39

Asp Val Tyr Leu Ala Val Ile Trp
1               5

<210> SEQ ID NO 40
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 40

Asp Val Phe Phe Ala Ala Ile Pro
1               5

<210> SEQ ID NO 41
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 41

Glu Ile Phe Leu Ala Val Ile Trp
1               5

<210> SEQ ID NO 42
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 42

Glu Ile Tyr Leu Glu Val Val Pro
1               5

<210> SEQ ID NO 43
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 43

Asp Ile Phe Leu Ala Val Ile Trp
1               5

<210> SEQ ID NO 44
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 44
```

```
Asp Ile Tyr Leu Glu Val Val Pro
  1               5
```

<210> SEQ ID NO 45
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 45

```
Glu Val Phe Leu Ala Val Ile Trp
  1               5
```

<210> SEQ ID NO 46
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 46

```
Glu Val Tyr Leu Glu Val Val Pro
  1               5
```

<210> SEQ ID NO 47
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 47

```
Asp Val Phe Leu Ala Val Ile Trp
  1               5
```

<210> SEQ ID NO 48
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 48

```
Asp Val Tyr Leu Glu Val Val Pro
  1               5
```

<210> SEQ ID NO 49
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 49

```
Glu Ile Tyr Phe Ala Val Ile Trp
  1               5
```

<210> SEQ ID NO 50
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 50

```
Glu Ile Phe Leu Glu Val Val Pro
  1               5
```

<210> SEQ ID NO 51
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 51

```
Asp Ile Phe Phe Ala Ala Val Trp
  1               5
```

<210> SEQ ID NO 52
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 52

```
Asp Ile Phe Leu Glu Val Val Pro
  1               5
```

<210> SEQ ID NO 53
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 53

```
Glu Val Phe Phe Ala Ala Val Trp
  1               5
```

<210> SEQ ID NO 54
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 54

```
Glu Val Phe Leu Glu Val Val Pro
  1               5
```

<210> SEQ ID NO 55
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 55

```
Asp Val Phe Phe Ala Ala Val Trp
  1               5
```

<210> SEQ ID NO 56
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 56

```
Asp Val Phe Leu Glu Val Val Pro
```

<210> SEQ ID NO 57
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 57

Glu Ile Tyr Leu Glu Val Ile Pro
 1               5

<210> SEQ ID NO 58
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 58

Asp Val Tyr Phe Glu Val Val Trp
 1               5

<210> SEQ ID NO 59
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 59

Asp Ile Tyr Leu Glu Val Ile Pro
 1               5

<210> SEQ ID NO 60
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 60

Glu Ile Phe Phe Glu Val Val Trp
 1               5

<210> SEQ ID NO 61
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 61

Glu Val Tyr Leu Glu Val Ile Pro
 1               5

<210> SEQ ID NO 62
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 62

Asp Ile Phe Phe Glu Val Val Trp
 1               5

```
<210> SEQ ID NO 63
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 63

Asp Val Tyr Leu Glu Val Ile Pro
 1               5

<210> SEQ ID NO 64
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 64

Glu Val Phe Phe Glu Val Val Trp
 1               5

<210> SEQ ID NO 65
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 65

Glu Ile Phe Leu Glu Val Ile Pro
 1               5

<210> SEQ ID NO 66
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 66

Asp Val Phe Phe Glu Val Val Trp
 1               5

<210> SEQ ID NO 67
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 67

Asp Ile Phe Leu Glu Val Ile Pro
 1               5

<210> SEQ ID NO 68
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 68

Glu Ile Tyr Leu Ala Val Val Trp
 1               5
```

```
<210> SEQ ID NO 69
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 69

Glu Val Phe Leu Glu Val Ile Pro
 1               5

<210> SEQ ID NO 70
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 70

Asp Ile Tyr Leu Ala Val Val Trp
 1               5

<210> SEQ ID NO 71
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 71

Asp Val Phe Leu Glu Val Ile Pro
 1               5

<210> SEQ ID NO 72
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 72

Glu Val Tyr Leu Ala Val Val Trp
 1               5

<210> SEQ ID NO 73
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 73

Glu Ile Tyr Phe Glu Val Ile Pro
 1               5

<210> SEQ ID NO 74
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 74

Asp Val Tyr Leu Ala Val Val Trp
 1               5
```

```
<210> SEQ ID NO 75
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 75

Asp Ile Tyr Phe Glu Val Ile Pro
 1               5

<210> SEQ ID NO 76
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 76

Glu Ile Phe Leu Ala Val Val Trp
 1               5

<210> SEQ ID NO 77
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 77

Glu Val Tyr Phe Glu Val Ile Pro
 1               5

<210> SEQ ID NO 78
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 78

Asp Ile Phe Leu Ala Val Val Trp
 1               5

<210> SEQ ID NO 79
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 79

Asp Val Tyr Phe Glu Val Ile Pro
 1               5

<210> SEQ ID NO 80
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 80

Glu Val Phe Leu Ala Val Val Trp
 1               5

<210> SEQ ID NO 81
```

<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 81

Glu Ile Phe Phe Glu Val Ile Pro
 1               5

<210> SEQ ID NO 82
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 82

Asp Val Phe Leu Ala Val Val Trp
 1               5

<210> SEQ ID NO 83
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 83

Asp Ile Phe Phe Glu Val Ile Pro
 1               5

<210> SEQ ID NO 84
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 84

Glu Ile Tyr Phe Ala Val Val Trp
 1               5

<210> SEQ ID NO 85
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 85

Glu Val Phe Phe Glu Val Ile Pro
 1               5

<210> SEQ ID NO 86
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 86

Asp Ile Tyr Phe Ala Val Val Trp
 1               5

<210> SEQ ID NO 87
<211> LENGTH: 8

```
<212> TYPE: PRT
<213> ORGANISM: Artificial Sequence
<220> FEATURE:
<223> OTHER INFORMATION: Beta-Secretase Cleavage Site

<400> SEQUENCE: 87

Asp Val Phe Phe Glu Val Ile Pro
 1               5

<210> SEQ ID NO 88
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 88

Glu Val Tyr Phe Ala Val Val Trp
 1               5

<210> SEQ ID NO 89
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 89

Glu Ile Tyr Leu Ala Val Ile Pro
 1               5

<210> SEQ ID NO 90
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 90

Asp Val Tyr Phe Ala Val Val Trp
 1               5

<210> SEQ ID NO 91
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 91

Asp Ile Tyr Leu Ala Val Ile Pro
 1               5

<210> SEQ ID NO 92
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 92

Glu Ile Phe Phe Ala Val Val Trp
 1               5

<210> SEQ ID NO 93
<211> LENGTH: 8
<212> TYPE: PRT
```

```
<213> ORGANISM: Artificial Sequence
<220> FEATURE:
<223> OTHER INFORMATION: Beta-Secretase Cleavage Site

<400> SEQUENCE: 93

Glu Val Tyr Leu Ala Val Ile Pro
 1               5

<210> SEQ ID NO 94
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 94

Asp Ile Phe Phe Ala Val Val Trp
 1               5

<210> SEQ ID NO 95
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 95

Asp Val Tyr Leu Ala Val Ile Pro
 1               5

<210> SEQ ID NO 96
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 96

Glu Val Phe Phe Ala Val Val Trp
 1               5

<210> SEQ ID NO 97
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 97

Glu Ile Phe Leu Ala Val Ile Pro
 1               5

<210> SEQ ID NO 98
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 98

Asp Val Phe Phe Ala Val Val Trp
 1               5

<210> SEQ ID NO 99
<211> LENGTH: 8
<212> TYPE: PRT
<213> ORGANISM: Artificial Sequence
```

```
<220> FEATURE:
<223> OTHER INFORMATION: Beta-Secretase Cleavage Site

<400> SEQUENCE: 99

Asp Ile Phe Leu Ala Val Ile Pro
 1               5

<210> SEQ ID NO 100
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 100

Glu Ile Tyr Leu Glu Ala Val Trp
 1               5

<210> SEQ ID NO 101
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 101

Glu Val Tyr Phe Ala Ala Val Pro
 1               5

<210> SEQ ID NO 102
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 102

Asp Ile Tyr Leu Glu Ala Val Trp
 1               5

<210> SEQ ID NO 103
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 103

Asp Val Tyr Phe Ala Ala Val Pro
 1               5

<210> SEQ ID NO 104
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 104

Glu Val Tyr Leu Glu Ala Val Trp
 1               5

<210> SEQ ID NO 105
<211> LENGTH: 8
<212> TYPE: PRT
<213> ORGANISM: Artificial Sequence
<220> FEATURE:
```

<223> OTHER INFORMATION: Beta-Secretase Cleavage Site

<400> SEQUENCE: 105

Glu Ile Phe Phe Ala Ala Val Pro
1               5

<210> SEQ ID NO 106
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 106

Asp Val Tyr Leu Glu Ala Val Trp
1               5

<210> SEQ ID NO 107
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 107

Asp Ile Phe Phe Ala Ala Val Pro
1               5

<210> SEQ ID NO 108
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 108

Glu Ile Tyr Phe Glu Val Val Pro
1               5

<210> SEQ ID NO 109
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 109

Glu Val Phe Phe Ala Ala Val Pro
1               5

<210> SEQ ID NO 110
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 110

Asp Ile Tyr Phe Glu Val Val Pro
1               5

<210> SEQ ID NO 111
<211> LENGTH: 8
<212> TYPE: PRT
<213> ORGANISM: Artificial Sequence
<220> FEATURE:
<223> OTHER INFORMATION: Beta-Secretase Cleavage Site

```
<400> SEQUENCE: 111

Asp Val Phe Phe Ala Ala Val Pro
1               5

<210> SEQ ID NO 112
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 112

Glu Val Tyr Phe Glu Val Val Pro
1               5

<210> SEQ ID NO 113
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 113

Asp Ile Tyr Phe Ala Val Ile Trp
1               5

<210> SEQ ID NO 114
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 114

Asp Val Tyr Phe Glu Val Val Pro
1               5

<210> SEQ ID NO 115
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 115

Glu Val Tyr Phe Ala Val Ile Trp
1               5

<210> SEQ ID NO 116
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 116

Glu Ile Phe Phe Glu Val Val Pro
1               5

<210> SEQ ID NO 117
<211> LENGTH: 8
<212> TYPE: PRT
<213> ORGANISM: Artificial Sequence
<220> FEATURE:
<223> OTHER INFORMATION: Beta-Secretase Cleavage Site
```

```
<400> SEQUENCE: 117

Asp Val Tyr Phe Ala Val Ile Trp
 1               5

<210> SEQ ID NO 118
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 118

Asp Ile Phe Phe Glu Val Val Pro
 1               5

<210> SEQ ID NO 119
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 119

Glu Ile Phe Phe Ala Val Ile Trp
 1               5

<210> SEQ ID NO 120
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 120

Glu Val Phe Phe Glu Val Val Pro
 1               5

<210> SEQ ID NO 121
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 121

Asp Ile Phe Phe Ala Val Ile Trp
 1               5

<210> SEQ ID NO 122
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 122

Asp Val Phe Phe Glu Val Val Pro
 1               5

<210> SEQ ID NO 123
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 123
```

Glu Val Phe Phe Ala Val Ile Trp
1               5

<210> SEQ ID NO 124
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 124

Glu Ile Tyr Leu Ala Val Val Pro
1               5

<210> SEQ ID NO 125
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 125

Asp Val Phe Phe Ala Val Ile Trp
1               5

<210> SEQ ID NO 126
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 126

Asp Ile Tyr Leu Ala Val Val Pro
1               5

<210> SEQ ID NO 127
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 127

Glu Ile Tyr Leu Glu Ala Ile Trp
1               5

<210> SEQ ID NO 128
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 128

Glu Val Tyr Leu Ala Val Val Pro
1               5

<210> SEQ ID NO 129
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 129

Asp Ile Tyr Leu Glu Ala Ile Trp
1               5

<210> SEQ ID NO 130
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 130

Asp Val Tyr Leu Ala Val Val Pro
1               5

<210> SEQ ID NO 131
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 131

Glu Val Tyr Leu Glu Ala Ile Trp
1               5

<210> SEQ ID NO 132
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 132

Glu Ile Phe Leu Ala Val Val Pro
1               5

<210> SEQ ID NO 133
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 133

Asp Val Tyr Leu Glu Ala Ile Trp
1               5

<210> SEQ ID NO 134
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 134

Asp Ile Phe Leu Ala Val Val Pro
1               5

<210> SEQ ID NO 135
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 135

Glu Ile Phe Leu Glu Ala Ile Trp

-continued

```
<210> SEQ ID NO 136
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 136

Glu Val Phe Leu Ala Val Val Pro
 1               5

<210> SEQ ID NO 137
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 137

Asp Ile Phe Leu Glu Ala Ile Trp
 1               5

<210> SEQ ID NO 138
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 138

Asp Val Phe Leu Ala Val Val Pro
 1               5

<210> SEQ ID NO 139
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 139

Glu Val Phe Leu Glu Ala Ile Trp
 1               5

<210> SEQ ID NO 140
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 140

Glu Ile Tyr Phe Ala Val Val Pro
 1               5

<210> SEQ ID NO 141
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 141

Asp Val Phe Leu Glu Ala Ile Trp
 1               5
```

<210> SEQ ID NO 142
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 142

Asp Ile Tyr Phe Ala Val Val Pro
 1               5

<210> SEQ ID NO 143
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 143

Glu Ile Tyr Phe Glu Ala Ile Trp
 1               5

<210> SEQ ID NO 144
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 144

Glu Val Tyr Phe Ala Val Val Pro
 1               5

<210> SEQ ID NO 145
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 145

Asp Ile Tyr Phe Glu Ala Ile Trp
 1               5

<210> SEQ ID NO 146
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 146

Asp Val Tyr Phe Ala Val Val Pro
 1               5

<210> SEQ ID NO 147
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 147

Glu Val Tyr Phe Glu Ala Ile Trp
 1               5

```
<210> SEQ ID NO 148
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 148

Glu Ile Phe Phe Ala Val Val Pro
 1               5

<210> SEQ ID NO 149
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 149

Asp Val Tyr Phe Glu Ala Ile Trp
 1               5

<210> SEQ ID NO 150
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 150

Asp Ile Phe Phe Ala Val Val Pro
 1               5

<210> SEQ ID NO 151
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 151

Glu Ile Phe Phe Glu Ala Ile Trp
 1               5

<210> SEQ ID NO 152
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 152

Glu Val Phe Phe Ala Val Val Pro
 1               5

<210> SEQ ID NO 153
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 153

Asp Ile Phe Phe Glu Ala Ile Trp
 1               5
```

```
<210> SEQ ID NO 154
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 154

Asp Val Phe Phe Ala Val Val Pro
 1               5

<210> SEQ ID NO 155
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 155

Glu Val Phe Phe Glu Ala Ile Trp
 1               5

<210> SEQ ID NO 156
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 156

Glu Ile Tyr Leu Glu Ala Val Pro
 1               5

<210> SEQ ID NO 157
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 157

Asp Val Phe Phe Glu Ala Ile Trp
 1               5

<210> SEQ ID NO 158
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 158

Glu Ile Phe Leu Glu Ala Val Trp
 1               5

<210> SEQ ID NO 159
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 159

Glu Ile Tyr Leu Ala Ala Ile Trp
 1               5

<210> SEQ ID NO 160
```

<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 160

Asp Ile Phe Leu Glu Ala Val Trp
  1               5

<210> SEQ ID NO 161
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 161

Asp Ile Tyr Leu Ala Ala Ile Trp
  1               5

<210> SEQ ID NO 162
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 162

Glu Val Phe Leu Glu Ala Val Trp
  1               5

<210> SEQ ID NO 163
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 163

Glu Val Phe Leu Ala Val Ile Pro
  1               5

<210> SEQ ID NO 164
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 164

Asp Val Phe Leu Glu Ala Val Trp
  1               5

<210> SEQ ID NO 165
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 165

Asp Val Phe Leu Ala Val Ile Pro
  1               5

<210> SEQ ID NO 166
<211> LENGTH: 8

```
<212> TYPE: PRT
<213> ORGANISM: Artificial Sequence
<220> FEATURE:
<223> OTHER INFORMATION: Beta-Secretase Cleavage Site

<400> SEQUENCE: 166

Glu Ile Tyr Phe Glu Ala Val Trp
 1               5

<210> SEQ ID NO 167
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 167

Glu Ile Tyr Phe Ala Val Ile Pro
 1               5

<210> SEQ ID NO 168
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 168

Asp Ile Tyr Phe Glu Ala Val Trp
 1               5

<210> SEQ ID NO 169
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 169

Asp Ile Tyr Phe Ala Val Ile Pro
 1               5

<210> SEQ ID NO 170
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 170

Glu Val Tyr Phe Glu Ala Val Trp
 1               5

<210> SEQ ID NO 171
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 171

Glu Val Tyr Phe Ala Val Ile Pro
 1               5

<210> SEQ ID NO 172
<211> LENGTH: 8
<212> TYPE: PRT
```

<213> ORGANISM: Artificial Sequence
<220> FEATURE:
<223> OTHER INFORMATION: Beta-Secretase Cleavage Site

<400> SEQUENCE: 172

Asp Val Tyr Phe Glu Ala Val Trp
1               5

<210> SEQ ID NO 173
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 173

Asp Val Tyr Phe Ala Val Ile Pro
1               5

<210> SEQ ID NO 174
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 174

Glu Ile Phe Phe Glu Ala Val Trp
1               5

<210> SEQ ID NO 175
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 175

Glu Ile Phe Phe Ala Val Ile Pro
1               5

<210> SEQ ID NO 176
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 176

Asp Ile Phe Phe Glu Ala Val Trp
1               5

<210> SEQ ID NO 177
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 177

Asp Ile Phe Phe Ala Val Ile Pro
1               5

<210> SEQ ID NO 178
<211> LENGTH: 8
<212> TYPE: PRT
<213> ORGANISM: Artificial Sequence

```
<220> FEATURE:
<223> OTHER INFORMATION: Beta-Secretase Cleavage Site

<400> SEQUENCE: 178

Glu Val Phe Phe Glu Ala Val Trp
 1               5

<210> SEQ ID NO 179
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 179

Glu Val Phe Phe Ala Val Ile Pro
 1               5

<210> SEQ ID NO 180
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 180

Asp Val Phe Phe Glu Ala Val Trp
 1               5

<210> SEQ ID NO 181
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 181

Asp Val Phe Phe Ala Val Ile Pro
 1               5

<210> SEQ ID NO 182
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 182

Glu Ile Tyr Leu Ala Ala Val Trp
 1               5

<210> SEQ ID NO 183
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 183

Glu Ile Tyr Leu Glu Ala Ile Pro
 1               5

<210> SEQ ID NO 184
<211> LENGTH: 8
<212> TYPE: PRT
<213> ORGANISM: Artificial Sequence
<220> FEATURE:
```

-continued

<223> OTHER INFORMATION: Beta-Secretase Cleavage Site

<400> SEQUENCE: 184

Asp Ile Tyr Leu Ala Ala Val Trp
1               5

<210> SEQ ID NO 185
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 185

Asp Ile Tyr Leu Glu Ala Ile Pro
1               5

<210> SEQ ID NO 186
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 186

Glu Val Tyr Leu Ala Ala Val Trp
1               5

<210> SEQ ID NO 187
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 187

Glu Val Tyr Leu Glu Ala Ile Pro
1               5

<210> SEQ ID NO 188
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 188

Asp Val Tyr Leu Ala Ala Val Trp
1               5

<210> SEQ ID NO 189
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 189

Asp Val Tyr Leu Glu Ala Ile Pro
1               5

<210> SEQ ID NO 190
<211> LENGTH: 8
<212> TYPE: PRT
<213> ORGANISM: Artificial Sequence
<220> FEATURE:
<223> OTHER INFORMATION: Beta-Secretase Cleavage Site

```
<400> SEQUENCE: 190

Glu Ile Phe Leu Ala Ala Val Trp
 1               5

<210> SEQ ID NO 191
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 191

Glu Ile Phe Leu Glu Ala Ile Pro
 1               5

<210> SEQ ID NO 192
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 192

Asp Ile Phe Leu Ala Ala Val Trp
 1               5

<210> SEQ ID NO 193
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 193

Asp Ile Phe Leu Glu Ala Ile Pro
 1               5

<210> SEQ ID NO 194
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 194

Glu Val Phe Leu Ala Ala Val Trp
 1               5

<210> SEQ ID NO 195
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 195

Glu Val Phe Leu Glu Ala Ile Pro
 1               5

<210> SEQ ID NO 196
<211> LENGTH: 8
<212> TYPE: PRT
<213> ORGANISM: Artificial Sequence
<220> FEATURE:
<223> OTHER INFORMATION: Beta-Secretase Cleavage Site
```

```
<400> SEQUENCE: 196

Asp Val Phe Leu Ala Ala Val Trp
1               5

<210> SEQ ID NO 197
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 197

Asp Val Phe Leu Glu Ala Ile Pro
1               5

<210> SEQ ID NO 198
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 198

Glu Ile Tyr Phe Ala Ala Val Trp
1               5

<210> SEQ ID NO 199
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 199

Glu Ile Tyr Phe Glu Ala Ile Pro
1               5

<210> SEQ ID NO 200
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 200

Asp Ile Tyr Phe Ala Ala Val Trp
1               5

<210> SEQ ID NO 201
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 201

Asp Ile Tyr Phe Glu Ala Ile Pro
1               5

<210> SEQ ID NO 202
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 202
```

```
Glu Val Tyr Phe Ala Ala Val Trp
1               5

<210> SEQ ID NO 203
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 203

Glu Val Tyr Phe Glu Ala Ile Pro
1               5

<210> SEQ ID NO 204
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 204

Asp Val Tyr Phe Ala Ala Val Trp
1               5

<210> SEQ ID NO 205
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 205

Asp Val Tyr Phe Glu Ala Ile Pro
1               5

<210> SEQ ID NO 206
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 206

Glu Ile Phe Phe Ala Ala Val Trp
1               5

<210> SEQ ID NO 207
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 207

Glu Ile Phe Phe Glu Ala Ile Pro
1               5

<210> SEQ ID NO 208
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 208
```

```
Asp Ile Tyr Leu Glu Ala Val Pro
 1               5

<210> SEQ ID NO 209
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 209

Asp Ile Phe Phe Glu Ala Ile Pro
 1               5

<210> SEQ ID NO 210
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 210

Glu Val Tyr Leu Glu Ala Val Pro
 1               5

<210> SEQ ID NO 211
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 211

Glu Val Phe Phe Glu Ala Ile Pro
 1               5

<210> SEQ ID NO 212
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 212

Asp Val Tyr Leu Glu Ala Val Pro
 1               5

<210> SEQ ID NO 213
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 213

Glu Val Tyr Leu Ala Ala Ile Trp
 1               5

<210> SEQ ID NO 214
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 214

Glu Ile Phe Leu Glu Ala Val Pro
```

<210> SEQ ID NO 215
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 215

Asp Val Tyr Leu Ala Ala Ile Trp
1               5

<210> SEQ ID NO 216
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 216

Asp Ile Phe Leu Glu Ala Val Pro
1               5

<210> SEQ ID NO 217
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 217

Glu Ile Phe Leu Ala Ala Ile Trp
1               5

<210> SEQ ID NO 218
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 218

Glu Val Phe Leu Glu Ala Val Pro
1               5

<210> SEQ ID NO 219
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 219

Asp Ile Phe Leu Ala Ala Ile Trp
1               5

<210> SEQ ID NO 220
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 220

Asp Val Phe Leu Glu Ala Val Pro
1               5

```
<210> SEQ ID NO 221
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 221

Glu Val Phe Leu Ala Ala Ile Trp
 1               5

<210> SEQ ID NO 222
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 222

Glu Ile Tyr Phe Glu Ala Val Pro
 1               5

<210> SEQ ID NO 223
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 223

Asp Val Phe Leu Ala Ala Ile Trp
 1               5

<210> SEQ ID NO 224
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 224

Asp Ile Tyr Phe Glu Ala Val Pro
 1               5

<210> SEQ ID NO 225
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 225

Glu Ile Tyr Phe Ala Ala Ile Trp
 1               5

<210> SEQ ID NO 226
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 226

Glu Val Tyr Phe Glu Ala Val Pro
 1               5
```

```
<210> SEQ ID NO 227
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 227

Asp Ile Tyr Phe Ala Ala Ile Trp
 1               5

<210> SEQ ID NO 228
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 228

Asp Val Tyr Phe Glu Ala Val Pro
 1               5

<210> SEQ ID NO 229
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 229

Glu Val Tyr Phe Ala Ala Ile Trp
 1               5

<210> SEQ ID NO 230
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 230

Glu Ile Phe Phe Glu Ala Val Pro
 1               5

<210> SEQ ID NO 231
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 231

Asp Val Tyr Phe Ala Ala Ile Trp
 1               5

<210> SEQ ID NO 232
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 232

Asp Ile Phe Phe Glu Ala Val Pro
 1               5
```

```
<210> SEQ ID NO 233
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 233

Glu Ile Phe Phe Ala Ala Ile Trp
 1               5

<210> SEQ ID NO 234
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 234

Glu Val Phe Phe Glu Ala Val Pro
 1               5

<210> SEQ ID NO 235
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 235

Asp Ile Phe Phe Ala Ala Ile Trp
 1               5

<210> SEQ ID NO 236
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 236

Asp Val Phe Phe Glu Ala Val Pro
 1               5

<210> SEQ ID NO 237
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 237

Glu Val Phe Phe Ala Ala Ile Trp
 1               5

<210> SEQ ID NO 238
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 238

Glu Ile Tyr Leu Ala Ala Val Pro
 1               5

<210> SEQ ID NO 239
```

```
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 239

Asp Val Phe Phe Ala Ala Ile Trp
 1               5

<210> SEQ ID NO 240
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 240

Asp Ile Tyr Leu Ala Ala Val Pro
 1               5

<210> SEQ ID NO 241
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 241

Glu Ile Tyr Leu Glu Val Val Trp
 1               5

<210> SEQ ID NO 242
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 242

Glu Val Tyr Leu Ala Ala Val Pro
 1               5

<210> SEQ ID NO 243
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 243

Asp Ile Tyr Leu Glu Val Val Trp
 1               5

<210> SEQ ID NO 244
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 244

Asp Val Tyr Leu Ala Ala Val Pro
 1               5

<210> SEQ ID NO 245
<211> LENGTH: 8
```

```
<212> TYPE: PRT
<213> ORGANISM: Artificial Sequence
<220> FEATURE:
<223> OTHER INFORMATION: Beta-Secretase Cleavage Site

<400> SEQUENCE: 245

Glu Val Tyr Leu Glu Val Val Trp
1               5

<210> SEQ ID NO 246
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 246

Glu Ile Phe Leu Ala Ala Val Pro
1               5

<210> SEQ ID NO 247
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 247

Asp Val Tyr Leu Glu Val Val Trp
1               5

<210> SEQ ID NO 248
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 248

Asp Ile Phe Leu Ala Ala Val Pro
1               5

<210> SEQ ID NO 249
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 249

Glu Ile Phe Leu Glu Val Val Trp
1               5

<210> SEQ ID NO 250
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 250

Glu Val Phe Leu Ala Ala Val Pro
1               5

<210> SEQ ID NO 251
<211> LENGTH: 8
<212> TYPE: PRT
```

```
<213> ORGANISM: Artificial Sequence
<220> FEATURE:
<223> OTHER INFORMATION: Beta-Secretase Cleavage Site

<400> SEQUENCE: 251

Asp Ile Phe Leu Glu Val Val Trp
 1               5

<210> SEQ ID NO 252
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 252

Asp Val Phe Leu Ala Ala Val Pro
 1               5

<210> SEQ ID NO 253
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 253

Glu Val Phe Leu Glu Val Val Trp
 1               5

<210> SEQ ID NO 254
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 254

Glu Ile Tyr Phe Ala Ala Val Pro
 1               5

<210> SEQ ID NO 255
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 255

Asp Val Phe Leu Glu Val Val Trp
 1               5

<210> SEQ ID NO 256
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 256

Asp Ile Tyr Phe Ala Ala Val Pro
 1               5

<210> SEQ ID NO 257
<211> LENGTH: 8
<212> TYPE: PRT
<213> ORGANISM: Artificial Sequence
```

```
<220> FEATURE:
<223> OTHER INFORMATION: Beta-Secretase Cleavage Site

<400> SEQUENCE: 257

Glu Val Asn Leu Asp Ala Glu Phe
 1               5

<210> SEQ ID NO 258
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 258

Glu Val Asn Leu Ala Ala Glu Phe
 1               5

<210> SEQ ID NO 259
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 259

Glu Val Asn Phe Ala Ala Glu Phe
 1               5

<210> SEQ ID NO 260
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 260

Glu Val Asn Phe Glu Ala Glu Phe
 1               5

<210> SEQ ID NO 261
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 261

Glu Val Asn Phe Ala Val Glu Phe
 1               5

<210> SEQ ID NO 262
<211> LENGTH: 8
<212> TYPE: PRT
<213> ORGANISM: Artificial Sequence
<220> FEATURE:
<223> OTHER INFORMATION: Beta-Secretase Cleavage Site

<400> SEQUENCE: 262

Glu Val Asn Phe Glu Val Glu Phe
 1               5

<210> SEQ ID NO 263
<211> LENGTH: 8
<212> TYPE: PRT
<213> ORGANISM: Artificial Sequence
<220> FEATURE:
```

```
<221> NAME/KEY: VARIANT
<222> LOCATION: (1)...(8)
<223> OTHER INFORMATION: Xaa = Cyclohexylglycine
<220> FEATURE:
<223> OTHER INFORMATION: Beta-Secretase Cleavage Site

<400> SEQUENCE: 263

Glu Val Asn Xaa Ala Ala Glu Phe
 1               5

<210> SEQ ID NO 264
<211> LENGTH: 8
<212> TYPE: PRT
<213> ORGANISM: Artificial Sequence
<220> FEATURE:
<221> NAME/KEY: VARIANT
<222> LOCATION: (1)...(8)
<223> OTHER INFORMATION: Xaa = Cyclohexylalanine
<220> FEATURE:
<223> OTHER INFORMATION: Beta-Secretase Cleavage Site

<400> SEQUENCE: 264

Glu Val Asn Xaa Ala Ala Glu Phe
 1               5
```

BETA-SECRETASE SUBSTRATES AND USES THEREOF

STATEMENT REGARDING FEDERALLY-SPONSORED R&D

Not applicable.

REFERENCE TO MICROFICHE APPENDIX

Not applicable.

FIELD OF THE INVENTION

The present invention relates generally to the field of neurological and physiological dysfunctions associated with Alzheimer's Disease. More particularly, the invention is concerned with the identification of peptides that act as substrates for β-secretase. The present invention also relates to methods of inhibiting the activity of β-secretase as well as to methods of screening for potential therapeutics for Alzheimer's Disease and to methods of treatment for Alzheimer's Disease. Methods for identifying compounds that modulate the activity of β-secretase are also provided.

BACKGROUND OF THE INVENTION

Few subjects in medicine today arouse the interest of the scientific community and the lay community as does Alzheimer's disease (AD). AD has emerged as the most prevalent form of late-life mental failure in humans. AD is a common dementing brain disorder of the elderly. The key features of the disease include progressive memory impairment, loss of language and visuospatial skills, and behavior deficits. These changes in cognitive function are the result of degeneration of neurons in the cerebral cortex, hippocampus, basal forebrain, and other regions of the brain. Neuropathological analyses of postmortem Alzheimer's diseased brains consistently reveal the presence of large numbers of neurofibrillary tangles in degenerated neurons and neuritic plaques in the extracellular space and in the walls of the cerebral microvasculature. The neurofibrillary tangles are composed of bundles of paired helical filaments containing hyperphosphorylated tau protein (Lee & Trojanowski, 1992, Curr. Opin. Neurobiol. 2:653–656). The neuritic plaques consist of deposits of proteinaceous material surrounding an amyloid core (Selkoe, 1994, Annu. Rev. Neurosci. 17:489–517).

AD has been estimated to affect more than 4 million people in the United States alone and perhaps 17 to 25 million worldwide. Moreover, the number of sufferers is expected to grow as the population ages. The pathology of AD has been studied extensively for the last 20 years, but it was not until about 15 years ago that the first molecular handle in understanding this complex degenerative disease was obtained, when the protein sequence of the extracellular amyloid was determined.

The effort to decipher the mechanism of AD has attracted the interest of investigators from diverse biological disciplines, including biochemistry, cell biology, molecular genetics, neuroscience, and structural biology. The eclectic nature of research approaches to AD and the intensity of scientific interest in the problem have made it increasingly likely that AD will become a premier example of the successful application of biological chemistry to the identification of rational therapeutic targets in a major human disease. Much of the recent progress in elucidating the pathogenesis of AD has centered on the apparent role of the 40–42-residue amyloid-protein (Aβ) as a unifying pathological feature of the genetically diverse forms of this complex disorder.

AD is divided into 2 classes: Familial AD, (FAD) which has an early onset and is heritable, and "non-familial", or sporadic AD (SAD), which has no identifiable cause. Although FAD is rare (less than 10% of all AD), the characteristic clinicopathological features—amyloid plaques, neurofibrillary tangles, synaptic and neuronal loss, and neurotransmitter deficits are apparently indistinguishable from the more common SAD.

The defining neuropathological characteristic of AD is the accumulation of insoluble proteinacious deposits, known as amyloid plaques, in the brains of those affected. The presence of these amyloid plaque deposits is the essential observation underpinning the amyloid hypothesis.

Evidence suggests that deposition of amyloid-β peptide (Aβ) plays a significant role in the development of amyloid plaques and the etiology of AD. For example, individuals with mutations in the gene encoding the β-amyloid precursor protein (APP) from which the Aβ protein is derived invariably develop Alzheimer's disease (Goate et al., 1991, Nature 353:844–846; Mullan et al., 1992, Nature Genet. 1:345–347; Murrell et al., 1991, Science 254:97–99; Van Broeckhoven, 1995, Eur. J. Neurol. 35:8–19). Likewise, autopsies have shown that amyloid plaques are found in the brains of virtually all Alzheimer's patients and that the degree of amyloid plaque deposition correlates with the degree of dementia (Cummings & Cotman, 1995, Lancet 326:1524–1587).

That increased expression and/or abnormal processing of APP is associated with the formation of amyloid plaques and cerebrovascular amyloid deposits, which are one of the major morphological hallmarks of AD has been corroborated from least two sources. The first is that transgenic mice which express altered APP genes exhibit neuritic plaques and age-dependent memory deficits (Games et al., 1995, Nature 373:523–525; Masliah et al., 1996, J. Neurosci. 16:5795–5811; Hsiao et al., 1996, Science 274:99–103).

The second body of evidence comes from study of patients suffering from Down's syndrome, who develop amyloid plaques and other symptoms of Alzheimer's disease at an early age (Mann & Esiri, 1989, J. Neurosci. 89:169–179). Because the APP gene is found on chromosome 21, it has been hypothesized that the increased gene dosage which results from the extra copy of this chromosome in Down's syndrome accounts for the early appearance of amyloid plaques (Kang et al., 1987, Nature 325:733–736; Tanzi et al., 1987, Science 235:880–884). Taken together with the evidence derived from cases of familial Alzheimer's disease, the current data suggest that genetic alterations which result in an increase in Aβ production can induce Alzheimer's disease. Accordingly, since Aβ deposition is an early and invariant event in Alzheimer's disease, it is believed that treatment which reduces production of Aβ will be useful in the treatment of this disease. Among the processes regulating APP metabolism, the proteolytic cleavage of APP into amyloidogenic or nonamyloidogenic fragments is of special interest.

The strongest evidence implicating Aβ in the pathogenesis of AD comes from the observation that Aβ peptides are toxic to neurons in culture and transgenic mice that overproduce Aβ in their brains show significant deposition of Aβ into amyloid plaques and significant neuronal toxicity (Yankner et al., 1989, Science 245:417–420; Frautschy et al., 1991, Proc. Natl. Acad. Sci. USA 88:8362–8366; Kowall et al., 1991, Proc. Natl. Acad. Sci. USA 88:7247–7251). This toxicity is enhanced if the peptides are "aged" (incubated from hours to days), a procedure that increases amyloid fibril formation. As well, injection of the insoluble, fibrillar form of Aβ into monkey brains results in the development of pathology (neuronal destruction, tau phosphorylation, microglial proliferation) that closely mimics Alzheimer's disease in humans (Geula et al., 1998, Nature Medicine 4:827–831). See Selkoe, 1994, J. Neuropathol. Exp. Neurol. 53:438–447 for a review of the evidence that amyloid plaques have a central role in Alzheimer's disease.

While abundant evidence suggests that extracellular accumulation and deposition of Aβ is a central event in the etiology of AD, recent studies have also proposed that increased intracellular accumulation of Aβ or amyloid containing C-terminal fragments may play a role in the pathophysiology of AD. For example, over-expression of APP harboring mutations which cause familial AD results in the increased intracellular accumulation of C100 in neuronal cultures and Aβ42 in HEK 293 cells. Aβ42 is the 42 amino acid long form of Aβ that is believed to be more efficacious at formed amyloid plaques than shorter forms of Aβ. Moreover, evidence suggests that intra- and extracellular Aβ are formed in distinct cellular pools in hippocampal neurons and that a common feature associated with two types of familial AD mutations in APP ("Swedish" and "London") is an increased intracellular accumulation of $A\beta_{42}$. Thus, based on these studies and earlier reports implicating extracellular Aβ accumulation in AD pathology, it appears that altered APP catabolism may be involved in disease progression.

APP is an ubiquitous membrane-spanning (type 1) glycoprotein that undergoes a variety of proteolytic processing events. (Selkoe, 1998, Trends Cell Biol. 8:447–453). APP is actually a family of peptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525–527; Tanzi et al., 1988, Nature 331:528–530; Kitaguchi et al., 1988, Nature 331:530–532). APP is expressed and constitutively catabolized in most cells.

APP has a short half-life and is metabolized rapidly down two pathways in all cells. The dominant catabolic pathway appears to be cleavage of APP within the Aβ sequence by α-secretase, resulting in the constitutive secretion of a soluble extracellular domain (sAPPα) and the appearance of a nonamyloidogenic intracellular fragment (approximately 9 kD), referred to as the constitutive carboxy-terminal fragment (cCTFα). cCTFα is a suitable substrate for cleavage by γ-secretase to yield the p3 fragment. This pathway appears to be widely conserved among species and present in many cell types (Weidemann et al., 1989, Cell 57:115–126; Oltersdorf et al., 1990, J. Biol. Chem. 265:4492–4497; and Esch et al., 1990, Science 248:1122–1124). In this pathway, processing of APP involves proteolytic cleavage at a site between residues $Lys_{16}$ and $Leu_{17}$ of the Aβ region while APP is still in the trans-Golgi secretory compartment (Kang et al., 1987, Nature 325:773–776). Since this cleavage occurs within the Aβ portion of APP, it precludes the formation of Aβ. sAPPα has neurotrophic and neuroprotective activities (Kuentzel et al., 1993, Biochem. J. 295: 367–378).

In contrast to this non-amyloidogenic pathway involving α-secretase described above, proteolytic processing of APP by β-secretase exposes the N-terminus of Aβ, which after γ-secretase cleavage at the variable C-terminus, liberates Aβ. This Aβ-producing pathway involves cleavage of the $Met_{671}$-$Asp_{672}$ bond (numbered according to the 770 amino acid isoform) by β-secretase. The C-terminus is actually a heterogeneous collection of cleavage sites rather than a single site since γ-secretase activity occurs over a short stretch of APP amino acids rather than at a single peptide bond. In the amyloidogenic pathway, APP is cleaved by β-secretase to liberate sAPPβ and CTFβ, which CTFβ is then cleaved by γ-secretase to liberate the harmful Aβ peptide.

Of key importance in this Aβ-producing pathway is the position of the γ-secretase cleavage. If the γ-secretase cut is at residue 711–712, short Aβ (Aβ40) is the result; if it is cut after residue 713, long Aβ (Aβ42) is the result. Thus, the γ-secretase process is central to the production of Aβ peptide of 40 or 42 amino acids in length (Aβ40 and Aβ42, respectively). For a review that discusses APP and its processing, see Selkoe, 1998, Trends Cell. Biol. 8:447453; Selkoe, 1994, Ann. Rev. Cell Biol. 10:373–403. See also, Esch et al., 1994, Science 248:1122.

Aβ, the principal component of amyloid plaques, is a 39–43 amino acid peptide which is capable of forming β-pleated sheet aggregates. These aggregating fibrils are subsequently deposited in the brain parenchyma or in the cerebrovasculature of the Alzheimer's disease victim (Glenner et al., 1984, Biochem. Biophys. Res. Comm. 120: 885–890; Masters et al., 1985, Proc. Natl. Acad. Sci. USA 82:4245–4249).

Reports show that soluble β-amyloid peptide is produced by healthy cells into culture media (Haass et al., 1992, Nature 359:322–325) and in human and animal CSF (Seubert et al., 1992, Nature 359:325–327).

Cleavage of APP can be detected in a number of convenient manners, including the detection of polypeptide or peptide fragments produced by proteolysis. Such fragments can be detected by any convenient means, such as by antibody binding. Another convenient method for detecting proteolytic cleavage is through the use of a chromogenic β-secretase substrate whereby cleavage of the substrate releases a chromogen, e.g., a colored or fluorescent, product.

Various groups have cloned and sequenced cDNA encoding a protein that is believed to be β-secretase (Vassar et al., 1999, Science 286:735–741; Hussain et al., 1999, Mol. Cell. Neurosci. 14:419–427; Yan et al., 1999, Nature 402:533–537; Sinha et al., 1999, Nature 402:537–540; Lin et al., 2000, Proc. Natl. Acad. Sci. USA 97:1456–1460). β-secretase has been called various names by these groups, e.g., BACE, Asp2, memapsin2.

Much interest has focused on the possibility of inhibiting the development of amyloid plaques as a means of preventing or ameliorating the symptoms of Alzheimer's disease. To that end, a promising strategy is to inhibit the activity of at least one of β- and γ-secretase, the two enzymes that together are responsible for producing Aβ. This strategy is attractive because, if the formation of amyloid plaques as a result of the deposition of Aβ is a cause of Alzheimer's disease, inhibiting the activity of one or both of the two secretases would intervene in the disease process at an early stage, before late-stage events such as inflammation or apoptosis occur. Such early stage intervention is expected to be particularly beneficial (see, e.g., Citron, 2000, Molecular Medicine Today 6:392–397).

Thus, it is believed that a drug that could interfere with β-amyloid plaque formation or toxicity may delay or halt the progression of Alzheimer's disease. At present, few suitable in vitro systems or methods exist for screening candidate drugs for the ability to inhibit or prevent the production of β-amyloid plaque. The scarcity of such screening methods may, at least in part, result from insufficient understanding of the pathogenic mechanism(s) which cause the conversion of amyloid precursor protein to the β-amyloid peptide, and ultimately to the amyloid plaque.

In view of the anticipated benefits of modulating APP catabolism as a treatment for diseases such as AD, compositions and methods for modulating APP catabolism in APP-containing cells which do not substantially alter the viability of those cells, have been desired and are addressed by the present invention.

For these reasons, it would be desirable to provide methods and systems for screening test compounds for the ability to inhibit or prevent the production of Aβ from APP. In particular, it would be desirable to base such methods and systems on a metabolic pathway which is involved in such conversion, where the test compound would be able to interrupt or interfere with the metabolic pathway which leads to conversion. In particular, initial methods should utilize in vitro systems rather than animal models, so that the methods are particularly suitable for initial screening of test compounds to identify suitable candidate drugs.

SUMMARY OF THE INVENTION

The present invention features 8-mer peptides that are suitable substrates for β-secretase, particularly human β-secretase. In vitro assays for measuring β-secretase activity employing such substrates are also disclosed. The peptide substrates are characterized as comprising at least one β-secretase cleavage site.

In one embodiment, the peptide substrates of the invention, when presented as an immunogen, elicit the production of a antibodies which specifically bind to a region of native APP having an amino acid sequence that is substantially homologous to that of any of the disclosed invention peptides. In another embodiment, the antibodies specifically bind the peptide substrates of the invention but do not specifically bind to native APP.

In another aspect of the present invention, antibodies are provided which are specific for an amino terminal fragment or carboxy terminal fragment (a/k/a cleavage product) of one of the peptides listed in Table 1 and/or Table 2 that results from cleavage of the substrates by β-secretase. The antibodies may be polyclonal or monoclonal.

In another aspect, the invention provides antibodies that recognize the synthetic β-secretase cleavage site of any of the 8-mer peptides listed in Table 1 and/or Table 2. In particular, antibodies that do not recognize the β-secretase cleavage site of native APP are provided.

An aspect of the present invention describes a nucleic acid comprising a nucleotide base sequence encoding any of the herein disclosed β-secretase substrates. Preferably, the nucleic acid is contained in an expression vector.

Another aspect of the present invention describes a recombinant cell comprising a nucleic acid encoding any of the disclosed β-secretase substrates or fragments thereof.

Another aspect of the present invention describes a method for assaying β-secretase activity. β-Secretase activity can be obtained from cells producing β-secretase in a solubilized form or in a membrane-bound form. The method can be performed by measuring cleavage product formation resulting from β-secretase substrate cleavage. Measuring can be performed by qualitative or quantitative techniques.

Thus an aspect of the present invention describes a method for measuring the ability of a compound to affect β-secretase activity comprising the steps of: (a) combining together a β-secretase substrate, a test compound, and a preparation comprising β-secretase activity, under reaction conditions allowing for β-secretase activity, and (b) measuring β-secretase activity.

An exemplary method utilizes a reaction system including β-secretase and a peptide substrate of the invention present in initial amounts. The reaction system is maintained under conditions which permit the β-secretase to cleave the peptide substrate into cleavage products. The β-secretase cleavage reaction is monitored by detecting the amount of at least one of the β-secretase cleavage products, where the amount of cleavage product(s) will increase over time as the reaction progresses. Such methods are particularly useful for screening test compounds for the ability to inhibit β-secretase activity. Test compounds are introduced to the reaction system, and the ability of the test compound to inhibit the β-secretase activity is determined based on the ability to decrease the amount of cleavage product produced, usually in comparison to a control where β-secretase mediated cleavage in the reaction system is observed and measured in the absence of test compound(s).

The methods of the present invention allow identification of test substances which inhibit proteolytic cleavage of to disclosed peptide substrates by β-secretase. The methods comprise exposing a peptide of the invention comprising a β-secretase cleavage site to β-secretase in the presence of the test substance under conditions such that the β-secretase would be expected to cleave the peptide substrate into an amino-terminal fragment and a carboxy-terminal fragment in the absence of the test substance. Test substances which inhibit such cleavage are thus identified as having β-secretase inhibition activity. Usually, generation of the amino-terminal fragment and/or the carboxy-terminal fragment is detected by an antibody specific for the carboxy end of the amino-terminal fragment or the amino end of the carboxy-terminal fragment. Alternative methods of detecting the amino-terminal and/or carboxyl-terminal fragments include liquid chromatography/mass spectrometry (LC/MS).

The present invention further comprises methods for inhibiting the cleavage of β-amyloid substrate in cells. Such methods comprise administering to the cells an amount of a compound effective to at least partially inhibit β-secretase activity. Usually, such compounds will be selected by the screening methods described above. Such compounds, will also find use in inhibiting binding of native or recombinant β-secretase to APP in vivo.

The present invention further provides methods for inhibiting the cleavage of β-amyloid precursor protein in mammalian hosts. Such methods comprise administering to the host an amount of a compound effective to inhibit β-secretase activity in cells of the host, usually in brain cells of the host. Such compounds will usually be selected by the screening assays described in this application. Such methods will be useful for treating conditions related to Aβ peptide deposition such as Alzheimer's disease, Down's syndrome, and the like.

In another aspect of the present invention, Aβ production inhibitors identified by the methods described herein may be studied in transgenic animal models. The animals are exposed to test compound(s) and those compounds which affect (usually by diminishing) the production of any of the cleavage products of APP are considered candidates for further testing as drugs for the treatment of Aβ-related conditions.

Methods and compositions are provided for detecting and monitoring an amino-terminal fragment resulting from β-secretase cleavage of any of the herein included peptide substrates. The resulting fragment, referred to as a an amino terminal cleavage product, βATF-PS (amino terminal fragment of the peptide substrates) may be detected in biological samples and is useful for monitoring the processing of the disclosed substrates in animal models. In particular, the present invention provides for monitoring in vivo processing of any of the disclosed peptide substrates where the presence of the βATF-PS is detected in a specimen from an animal transformed to express the substrates and where the βATF-PS has been cleaved from the substrate between amino acids 596 and 597, based on the numbering of Kang et al., 1987, Nature 325:733–736 in the 695 amino acid isoform.

It has been found that cells expressing the gene encoding any of the herein disclosed peptide substrates are particularly prolific producers of the cleavage products of said peptide substrate that are the amino- and the carboxy-terminal fragments thereof. That is, such cells are able to cleave the substrates of the invention at a greater frequency than cleavage of either the endogenous APP, the wild type human APP, or the Swedish mutant APP. It is further believed that intracellular processing of the substrates of the invention results in greater production of the βATF-PS than is produced by other human mutations of the APP gene. Thus, transgenic animal systems, such as transgenic mice, expressing any of the herein disclosed peptide substrates are particularly suitable as models for monitoring intracellular processing of the disclosed substrates as well as for screening test compounds for the ability to inhibit or modulate cleavage of APP as a result of β-secretase activity, the apparently pathogenic form of APP processing.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 depicts peptide libraries derived from Swedish mutant APP. The amino acids are represented in single letter code. SEQ ID NO: 257 (top row) represents Swedish mutant APP corresponding to amino acids 593–560 based upon numbering of the 695 isoform of APP.

DETAILED DESCRIPTION OF THE INVENTION

Figure 2:
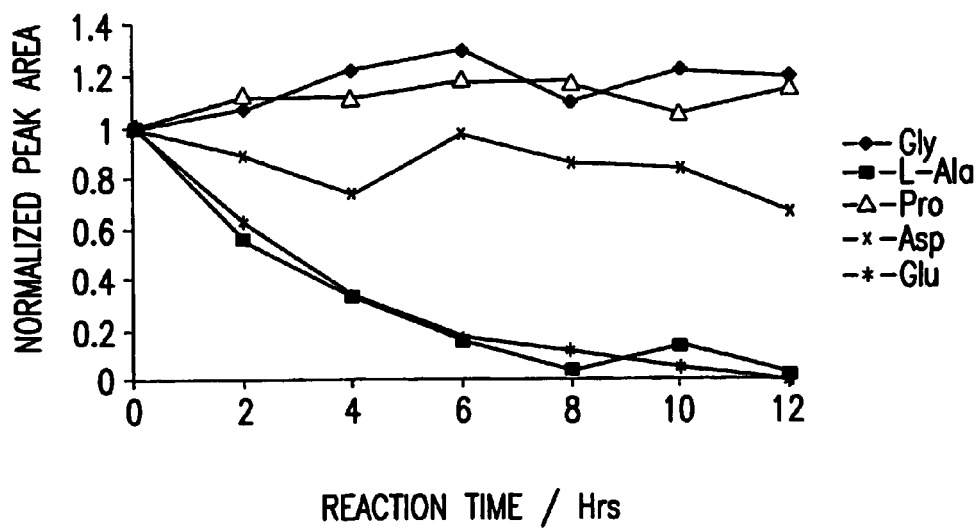
FIG. 2 depicts data illustrating the differences in rates of cleavage of the various peptide substrates from the P1 library by β-secretase.

As used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

The present invention features β-secretase substrates and assays for detecting β-secretase activity employing such substrates. The β-secretase substrate can be cleaved by β-secretase activity.

Assaying for β-secretase activity can be used, for example, to screen for compounds able to modulate β-secretase activity, and to test the ability of a particular compound to affect β-secretase activity. Examples of compounds able to modulate β-secretase activity include β-secretase inhibitors. Inhibitors can be employed for different purposes, such as in the treatment of Alzheimer's disease or characterization of the biological importance of β-secretase.

Provided herein are numerous synthetic 8-mer peptides, each comprising a synthetic β-secretase cleavage site. Table 2 lists 256 8-mer peptide substrate sequences that are substrates for β-secretase, particularly human β-secretase. Polynucleotides encoding the peptide substrate sequences and methods employing the peptide substrate sequences in assays to identify compounds that inhibit the proteolytic activity of β-secretase, native or recombinant, in vitro or in vivo, are also within the scope of the present invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

All publications mentioned herein are incorporated herein by reference for the purpose of describing and disclosing the methodologies, vectors, etc. which are reported in the publications that might be used in connection with the invention. Nothing herein is to be construed as an admission that the invention is not entitled to antedate such disclosures by virtue of prior invention.

In the description that follows, a number of terms used in the field of recombinant DNA technology are extensively utilized. In order to provide a clearer and consistent understanding of the specification and claims, including the scope to be given such terms, the following definitions are provided.

Use of the terms "isolated" and/or "purified" in the present specification and claims as a modifier of DNA, RNA, polypeptides, peptides, or proteins means that the DNA, RNA, polypeptides, peptides, or proteins so designated have been produced in such form by the hand of man, and thus are separated from their native in vivo cellular environment. As a result of this human intervention, the recombinant DNAs, RNAs, polypeptides, peptides, or proteins of the invention are useful in ways described herein that the DNAs, RNAs, polypeptides, peptides, or proteins as they naturally occur are not. A peptide that has been produced by synthetic means, e.g., by the solid phase chemistry disclosed herein, and that is the predominant peptide species present, is an "isolated" or "purified" peptide.

Similarly, as used herein, "recombinant" as a modifier of DNA, RNA, polypeptides, peptides, or proteins means that the DNA, RNA, polypeptides, peptides, or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

An "insertion" or "addition," as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

A "disorder" is any condition that would benefit from treatment with (1) the disclosed invention peptides (2) antibodies specific for each of the disclosed invention peptides (3) or any compound that inhibits the proteolytic activity of β-secretase. This includes chronic and acute disorders or diseases including those pathological conditions which predispose the mammal to the disorder in question. Disorders include Alzheimer's Disease.

"Antagonist" or "inhibitor" as used herein refers to an agent that downregulates (e.g., suppresses or inhibits) at least one β-secretase bioactivity. A β-secretase inhibitor can be a compound or molecule which inhibits or decreases the interaction between a β-secretase and its binding partner, e.g., native or mutant APP or any one of the disclosed invention peptides. A compound that decreases the rate at which β-secretase cleaves its substrate is a β-secretase inhibitor.

The term "modulation" is used herein to refer to the capacity to inhibit a biological or functional activity, e.g., proteolytic activity and/or pharmacological activity of human β-secretase.

"Substantially similar" indicates a sequence similarity of at least about 80% to a reference sequence. In different embodiments the sequence similarity is at least about 90%, at least about 95% or 100%. Sequence similarity can be determined using techniques well known in the art, such as those described by Altschul et al., 1997, Nucleic Acids Res. 25:3389–3402, hereby incorporated by reference herein.

"Direct administration" as used herein refers to the direct administration of antibodies specific for any of the herein disclosed invention peptides or functional derivatives thereof that inhibit the proteolytic activity of human β-secretase. Compounds that achieve an inhibitory effect are also included.

A "β-CTF domain" is a polypeptide that can be cleaved by γ-secretase and which approximates the C-terminal fragment (amino acids 597–695) of APP produced after cleavage of APP by a β-secretase, or is a functional derivative thereof.

As used herein, "β-amyloid peptide (Aβ)" refers to any of the β-amyloid peptides. Such peptides are typically about 4 kD. Several different amino-termini and heterogeneous carboxyl-termini sequences have been observed based on characterization of Aβ from Alzheimer's disease tissue and from cultured cells (Glenner & Wong, 1984, Biochem. Biophys. Res. Comm. 120:885–890; Joachim et al., 1988, Brain Res. 474:100–111; Prelli et al., 1988, J. Neurochem. 51:648–651; Mori et al., 1992, J. Biol. Chem. 267:17082–17806; Seubert et al., 1992, Nature 359:325–327; Naslund et al., 1994, Proc. Natl. Acad. Sci. USA 91:8378–8382; Roher et al., 1993, Proc. Natl. Acad. Sci. USA 90:10836–10840; Busciglio et al., 1993, Proc. Natl. Acad. Sci. USA 90:2092–2096; Haass et al., 1992, Nature 359:322–325). With regard to the carboxyl-termini, Aβ has been shown to end at position 39, 40, 41, 42, 43, or 44 where position 1 is the aspartate of the Aβ sequence of SEQ ID NO: 257. Aβ is produced by the processing of APP including cleavage at both the amino-terminus and carboxy-terminus of the Aβ region of APP.

As used herein, "β-amyloid precursor protein (APP)" refers to a protein that is encoded by a gene of the same name localized in humans on the long arm of chromosome 21 and that includes the Aβ region within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al., 1987, Nature 325: 733–736; a 751-amino acid polypeptide described by Ponte et al., 1988, Nature 331:525–527 and Tanzi et al., 1988, Nature 331:528–530; as well as a 770-amino acid isotype of APP described in Kitaguchi et al., 1988, Nature 331:530–532. A number of specific variants of APP have also been described having point mutations which can differ in both position and phenotype. A general review of such mutations is provided in Hardy, 1992, Nature Genet. 1:233–234. A mutation of particular interest is designated the "Swedish" mutation where the normal Lys-Met residues at positions 595 and 596 of the 695 form are replaced by Asn-Leu. This mutation is located directly upstream of the normal β-secretase cleavage site of APP, which occurs between residues 596 and 597 of the 695 form. SEQ ID NO: 257 shows the amino acid sequence of the Swedish mutant in the region of the β-secretase cleavage site.

As used herein, the term "human β-secretase," and "β-secretase" refers to a protein/enzyme, that exhibits the same properties as that attending native β-secretase, i.e., ability to cleave APP and yield the amino terminus of Aβ peptide that is the main component of the amyloid plaques found in patients suffering from Alzheimer's disease.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "recombinant protein" refer to a protein that is produced by expression of a nucleotide sequence encoding the amino acid sequence of the protein from a recombinant DNA molecule.

A "functional derivative thereof" has a sufficient sequence similarity to the invention peptide amino acid sequences such that it can be cleaved by β-secretase. Examples of modifications to the invention peptide substrates that can produce a functional derivative include additions, deletions, and substitutions. The effect of a particular modification can be measured using reaction conditions described herein that allow for β-secretase cleavage of a β-secretase substrate. Preferred modifications do not cause a substantial decrease in activity.

Substitutions in the substrate not causing a substantial decrease in activity can be initially designed taking into account differences in naturally occurring amino acid R groups. An R group effects different properties of the amino acid such as physical size, charge, and hydrophobicity. Amino acids can be divided into different groups as follows: neutral and hydrophobic (alanine, valine, leucine, isoleucine, proline, tryptophan, phenylalaine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids, it is preferable to exchange amino acids having similar properties. Substituting different amino acids within a particular group, such as substituting valine for leucine, arginine for lysine, and asparagine for glutamine is likely to not cause a change in peptide functioning.

Changes outside of different amino acid groups can also be made. Preferably, such changes are made taking into account the position of the amino acid to be substituted in the peptide. For example, arginine can substitute more freely for nonpolar amino acids in the interior of a polypeptide then glutamate because of its long aliphatic side chain. (See, Ausubel, *Current Protocols in Molecular Biology*, John Wiley, 1987–1998, Supplement 33, Appendix 1C).

An amino acid sequence or a nucleotide sequence is "identical" to a reference sequence if the two sequences are the same when aligned for maximum correspondence over a comparison window. Optimal alignment of nucleotide and amino acid sequences for aligning comparison window may be conducted by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Natl. Acad. Sci., U.S.A. 85:2444–2448, by computerized implementations of these algorithms (GAP, BESFIT, FASTA, and TFASTA in the Wisconsin Genetics Software Package Release 7.0, Genetics Computer Group, 575 Science Dr., Madison, Wis. , or by inspection. "Consists essentially," with respect to a β-secretase substrate, indicates that the reference sequence can be modified by N-terminal and/or C-terminal additions or deletions that do not cause a substantial decrease in the ability of the β-secretase substrate to be cleaved compared to the reference sequence. An example of a deletion is the removal of an N-terminal methionine.

A substantial decrease in the ability of the β-secretase substrate to be cleaved is a decrease of 10 fold or more compared to activity observed using a reference substrate incubated with appropriate buffers and suitable reagents.

As used herein, "test compounds" may be any substance, molecule, compound, mixture of molecules or compounds, or any other composition which is suspected of being capable of inhibiting β-secretase activity in vivo or in vitro. The test compounds may be macromolecules, such as biological polymers, including proteins, polysaccharides, nucleic acids, or the like. More usually, the test compounds will be small molecules having a molecular weight below about 2 kD, more usually below 1.5 kD, frequently below 1 kD, and usually in the range from 100 to 1,000 D, and even more usually in the range from 200 D to 750 D. Such test compounds may be preselected based on a variety of criteria. For example, suitable test compounds may be selected as having known proteolytic inhibition activity. Alternatively, the test compounds may be selected randomly and tested by the screening methods of the present invention. Test compounds which are able to inhibit β-secretase cleavage of the invention peptide substrates in vitro are considered as candidates for further screening of their ability to decrease Aβ production in cells and/or animals.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. These include, e.g., Fab' and F(ab)'2 fragments. The term "antibody" also includes antibody fragments either produced by the modification of whole antibodies or those synthesized de novo using recombinant DNA methodologies, and further includes "humanized" antibodies made by conventional techniques.

The term "immunoassay" is an assay that utilizes an antibody to specifically bind an analyte. The immunoassay is characterized by the use of specific binding properties of a particular antibody to isolate, target, and/or quantify the analyte.

An antibody "specifically binds to" or "is specifically immunoreactive with" a protein, polypeptide, or peptide when the antibody functions in a binding reaction which is determinative of the presence of the protein, polypeptide, or peptide in the presence of a heterogeneous population of proteins and other biologics. Thus, under designated immunoassay conditions, the specified antibodies bind preferentially to a particular protein, polypeptide, or peptide and do not bind in a significant amount to other proteins, polypeptides, or peptides present in the sample. Specific binding to a protein, polypeptide, or peptide under such conditions requires an antibody that is selected for specificity for a particular protein, polypeptide, or peptide. A variety of immunoassay formats may be used to select antibodies specifically immunoreactive with a particular protein, polypeptide, or peptide. For example, solid-phase ELISA immunoassays are routinely used to select monoclonal antibodies specifically immunoreactive with a protein, polypeptide, or peptide. See Harlow & Lane, 1988, Antibodies, A Laboratory Manual, Cold Spring Harbor Publications, New York, for a description of immunoassay formats and conditions that can be used to determine specific immunoreactivity.

Antibodies, including binding fragments and single chain recombinant versions thereof, against the invention peptides are raised by immunizing animals, e.g., with conjugates of the peptides with carrier proteins as described above. It is understood that antibodies raised against any of the invention peptides may bind native or mutant APP. However, of special interest are antibodies raised against any of the invention peptides that do not bind native or mutant APP but that do bind the peptide of the invention.

The peptide substrates of the present invention may be used to prepare polyclonal and/or monoclonal antibodies using conventional techniques. The intact invention peptide, optionally coupled to a carrier molecule, may be injected into small vertebrates, with monoclonal antibodies being produced by well-known methods, as described in detail below. Antibodies so produced will be useful for performing conventional immunoassays to detect peptides of the invention in biological and other specimens. Antibodies according to the present invention will bind to the invention peptides with high affinity of at least $10^6$ $M^{-1}$. Likewise, the cleavage products produced as a result of the cleavage of the invention peptides by β-secretase can also be used as immunogens for the production of antibodies specific thereto.

A recombinant invention peptide, or a synthetic version thereof, may be injected into an animal capable of producing antibodies. Either monoclonal or polyclonal antibodies can be generated for subsequent use in immunoassays to measure the presence and quantity of the peptide.

Methods of producing polyclonal antibodies are known to those of skill in the art. In brief, an immunogen, preferably an invention peptide, an invention peptide coupled to an appropriate carrier (e.g., GST, keyhole limpet hemanocyanin, etc.) or incorporated into an immunization vector such as a recombinant vaccinia virus (see, e.g., U.S. Pat. No. 4,722,848) is mixed with an adjuvant and animals are immunized with the mixture. The animal's immune response to the immunogen preparation is monitored by taking test bleeds and determining the titer of reactivity to the peptide of interest. When approximately high titers of antibody to the immunogen are obtained, blood is collected from the animal and antisera are prepared. Further fractionation of the antisera to enrich for antibodies reactive to the peptide is performed where desired. See, e.g., Coligan, 1991, Current Protocols in Immunology Wiley/Greene, NY; and Harlow & Lane, 1989, Antibodies: A Laboratory Manual Cold Spring Harbor Press, NY.

Monoclonal antibodies may be prepared from cells secreting the desired antibody. In some instances, it is desirable to prepare monoclonal antibodies from particular mammalian hosts, such as mice, rodents, primates, humans, etc. Description of techniques for preparing such monoclonal antibodies are found in, e.g., Stites et al., eds., Basic and Clinical Immunology, 4th ed., Lange Medical Publications, Los Altos, Calif., and references cited therein; Harlow & Lane, supra; Goding, 1986, Monoclonal Antibodies: Principles and Practice (2d ed.) Academic Press, New York, N.Y.; and Kohler & Milstein, 1975, Nature 256:495–497. This method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and the yield of the monoclonal antibodies produced by such cells is enhanced by various techniques, including injection into the peritoneal cavity of a vertebrate (preferably mammalian) host. The antibodies of the present invention are used with or without modification, and include chimeric antibodies such as humanized murine antibodies.

Other suitable techniques involve selection of libraries of recombinant antibodies in phage or similar vectors. See, Huse et al., 1989, Science 246:1275–1281; and Ward et al., 1989, Nature 341: 544–546.

Frequently, the peptides and antibodies will be labeled by joining, either covalently or non covalently, a substance which provides for a detectable signal. A wide variety of labels and conjugation techniques are know and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,272,149; and U.S. Pat. No. 4,366,241. Also, recombinant immunoglobulins may be produced. See, Cabilly, U.S. Pat. No. 4,816,567; and Queen et al., 1989, Proc. Natl. Acad. Sci. USA 86:10029–10033.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available. A label often generates a measurable signal, such as radioactivity, fluorescent light or enzyme activity, which can be used to quantitate the amount of bound label.

Labels can be attached directly or via spacer arms of various lengths (to reduce steric hindrance). Any of a wide variety of labeled reagents can be used for purposes of the present invention. For instance, one or more labeled nucleoside triphosphates, primers, linkers, or probes can be used. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference.

The term label can also refer to a "tag", which can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect the presence of HRP. In a similar fashion, the tag can be an epitope or antigen (e.g., digoxigenin), and an enzymatically, fluorescently, or radioactively labeled antibody can be used to bind to the tag.

The antibodies of this invention are also used for affinity chromatography in isolating the invention peptides. Columns are prepared, e.g., with the antibodies linked to a solid support, e.g., particles, such as agarose, Sephadex, or the like, where a sample suspected of containing the invention peptides or even native APP is passed through the column, washed and treated with increased concentrations of a mild denaturant, whereby invention peptides or the subject APP proteins are released.

The antibodies can be used to screen expression libraries for particular expression products such as mammalian APP, preferably bound to β-secretase. Usually the antibodies in such a procedure are labeled with a moiety allowing easy detection of presence of antigen by antibody binding.

An alternative approach is the generation of humanized immunoglobulins by linking the CDR regions of the non-human antibodies to human constant regions by recombinant means. The humanized immunoglobulins have variable region framework residues substantially from a human immunoglobulin (termed an acceptor immunoglobulin) and complementarity determining regions substantially from a mouse immunoglobulin (referred to as the donor immunoglobulin). The constant region(s), if present, are also substantially from a human immunoglobulin. The human variable domains are usually chosen from human antibodies whose framework sequences exhibit a high degree of sequence identity with the murine variable region domains from which the CDRs are derived. The heavy and light chain variable region framework residues can be derived from the same or different human antibody sequences. The human antibody sequences can be the sequences of naturally occurring human antibodies or can be consensus sequences of several human antibodies. See International Patent Publication WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

Other candidates for substitution are acceptor human framework amino acids that are unusual for a human immunoglobulin at that position. These amino acids can be substituted with amino acids from the equivalent position of the antibody or from the equivalent positions of more typical human immunoglobulins.

A further approach for isolating DNA sequences which encode a human monoclonal antibody or a binding fragment thereof is by screening a DNA library from human B cells according to the general protocol outlined by Huse et al., 1989, Science 246:1275–1281 and then cloning and amplifying the sequences which encode the antibody (or binding fragment) of the desired specificity. The protocol described by Huse is rendered more efficient in combination with phage display technology. See, e.g., International Patent Publication WO 91/17271 and International Patent Publication WO 92/01047. Phage display technology can also be used to mutagenize CDR regions of antibodies previously shown to have affinity for β-secretase protein receptors or their ligands. Antibodies having improved binding affinity are selected.

An aspect of the invention provides methods for identifying compounds which diminish or abolish interaction of β-secretase with its native substrate. The invention peptides may be employed in a competitive binding assay. Such an assay can accommodate the rapid screening of a large number of compounds to determine which compounds, if any, are capable of inhibiting the binding of human β-secretase to a substrate. Subsequently, more detailed assays can be carried out with those compounds found to bind, to further determine whether such compounds act as inhibitors of human β-secretase cleavage activity.

As understood by those of skill in the art, assay methods for identifying compounds that modulate proteolytic activity of β-secretase generally require comparison to a control. One type of control is a cell or culture that is treated substantially the same as the test cell or test culture exposed to the compound, with the distinction that the control cell or culture is not exposed to the compound.

Alternatively, a control system mayinclude a peptide substrate modified from any of those disclosed herein which effectively is NOT cleaved by human β-secretase.

Another type of control cell or culture may be a cell or culture that is identical to the transfected cells, with the exception that the control cell or culture do not express the invention peptide. Accordingly, the response of the transfected cell to compound is compared to the response (or lack thereof) of the control cell or culture to the same compound under the same reaction conditions.

"Treatment" refers to both therapeutic treatment and prophylactic or preventative measures. Those in need of treatment include those already with the disorder as well as those prone to have the disorder or those in which the disorder is to be prevented.

By "screening" is meant investigating a collection of substances (e.g., test compounds) for the presence or absence of a property. Screening may include measuring or detecting various properties, including the level of inhibition of β-secretase or the level of interaction between a β-secretase and its substrate.

By "therapeutically effective amount" is meant an amount of a pharmaceutical composition that relieves to some extent one or more symptoms of the disease or condition in the patient (e.g., prevents formation or additional deposit of amyloid plaques) or returns to normal either partially or completely one or more physiological or biochemical parameters associated with or causative of the disease or condition.

An alternative embodiment of the invention provides a method for treatment of Alzheimer's disease which comprises administering to a patient an effective amount of a therapeutic compound which is capable eof inhibiting the cleavage of native APP in said patient and thereby preventing the increased deposition of amyloid plaque in said patient.

Provided herein are nucleic acid molecules comprising a sequence of nucleotides that encode any one of the herein disclosed invention peptides. DNA sequences encoding any one or more of the herein disclosed peptides can be used for recombinantly producing the invention peptides when such nucleic acids are incorporated into a variety of protein expression systems known to those of skill in the art.

The term "nucleic acid" refers to a deoxyribonucleotide or ribonucleotide polymer in either single- or double-stranded form, and, unless otherwise limited, encompasses known analogs of natural nucleotides that can function in a similar manner as naturally occurring nucleotides. It will be understood that when a nucleic acid molecule is said to have a DNA sequence, this also includes RNA molecules having the corresponding RNA sequence in which "U" replaces "T".

The term "recombinant host cell" refers to a cell having DNA introduced from an exogenous source. Thus, for example, recombinant host cells may express genes that are not found within the native (non-recombinant) form of the cell or may express genes normally found in the cell but which have been introduced into the cell in a different manner, e.g., linked to different expression control sequences.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al., 1989, Molecular *Cloning: A Laboratory Manual*, Second Edition, Cold Spring Harbor Laboratory Press). Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, 1989, Science, 244:1275–1281; Mulligan, 1993, Science, 260: 926–932, each of which are incorporated herein by reference in their entirety).

Thus, an embodiment of the present invention provides transformed host cells that recombinantly express the herein disclosed invention peptides.

As used herein, a cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

Provided by the present invention are isolated, purified, and/or substantially pure peptide substrates (invention peptides) which are listed in Table 1 and Table 2. Functionally equivalent derivatives of the herein disclosed peptides are also included as part of the invention. Such derivatives are those that have minor substitutions in their amino acid sequences, but which are nonetheless as effective as the native invention peptides from which each was derived. Thus, functionally equivalent peptides have the ability to act as substrates for β-secretase.

"Invention peptide" or "invention peptide substrate" or "peptide substrate sequences" or "peptide substrate" are used interchangeably to refer to a non-naturally occurring peptide comprising a contiguous sequence fragment of at least 8 amino acids, and which comprises a synthetic β-secretase cleavage site, where the at least 8 amino acids have a sequence selected from the group consisting of: SEQ ID NOs: 1–256, 258–263, and 264. Fragments and homologs thereof are also intended to be encompassed by the present invention.

The invention peptide substrates are characterized as comprising a sequence of amino acids that is not only a suitable substrate for β-secretase cleavage but also is hydrolyzed at a rate that is substantially faster than that attending a peptide derived from the corresponding region of Swedish mutant APP (SEQ ID NO: 257). Some of the substrates are cleaved at rates 33 times faster than the Swedish mutant APP. One substrate, EVNFEVEF (SEQ ID NO: 262), is cleaved at a rate 60 times faster than the Swedish mutant APP.

Active invention peptide substrate analogs/fragments include peptide analogs whose amino acid sequence differs from those of either Table 1 or Table 2 by the inclusion of amino acid substitutions, additions or deletions (e.g., active fragments). Active fragments can be identified by empirically testing the resulting analogs for activity.

Active analogs bearing substitutions can be prepared by introducing selected amino acid substitutions into a peptide. Any substitutions where the activity is maintained or enhanced will be within the present invention, but usually the substitutions will be "conservative" as defined herein. The number of substitutions is at the discretion of the practitioner, but the amino acid sequence of the resulting peptide must conform to the definition of active peptide. Conservative amino acid substitutions refer to the potential interchangeability of residues having similar side chains. For example, a group of amino acids having aliphatic side chains is glycine, alanine, valine, leucine, and isoleucine; a group of amino acids having aliphatic-hydroxyl side chains includes serine and threonine; a group of amino acids having acidic side chains includes aspartic acid and glutamic acid; a group of amino acids having basic side chains includes lysine, arginine, and histidine; and a group of amino acids having sulfur-containing side chains includes cysteine and methionine. Preferred conservative amino acids substitution groups are: valine-leucine-isoleucine, phenylalanine-tyrosine, lysine-arginine, alanine-valine, and asparagine-glutamine.

The invention peptides, biologically active fragments, and functional equivalents thereof can be produced by chemical synthesis. For example, synthetic peptides can be produced using Applied Biosystems, Inc. Model 430A or 431A automatic peptide synthesizer (Foster City, Calif.) employing the chemistry provided by the manufacturer.

The invention peptides may also be in the form of fusion polypeptides where the invention peptide is joined to all or a portion of another protein. Fusions may be generated with heterologous proteins (for example, a reporter polypeptide, a binding polypeptide, or the like). Fusion polypeptides may be formed either recombinantly or by synthetic methods which are well-known in the art.

The peptides of the present invention may also have amino acid residues which have been chemically modified by known techniques, such as phosphorylation, sulfonation, biotinylation or the addition of other moieties. In some embodiments, the modifications will be useful for labeling reagents, purification targets, affinity ligand targeting, or the like.

As used herein, substrate activity of human β-secretase refers to any activity characteristic of β-secretase. Such activity can typically be measured by one or more in vitro methods, and frequently corresponds to an in vivo activity of the secretase enzyme. Such activity may be measured by any method known to those of skill in the art, such as, for example, assays that measure liberation of cleavage products, e.g., N or C-terminal fragments of the invention peptide substrates.

See Table 2 for a list of available invention peptide substrates that are cleaved by human β-secretase. Based upon the sequences provided herein, additional substrates can be identified and designed using known techniques.

The present invention further provides assays for detecting β-secretase mediated cleavage of peptide substrates such as those exemplified in Table 2. The methods utilize a reaction system which includes (i) a β-secretase component and (ii) a substrate component, preferably the invention peptide, where the β-secretase cleaves the substrate over time to produce cleavage products. Thus, β-secretase activity can be observed and monitored over time as the amount of cleavage product(s) increases. The amount of cleavage product(s) in the reaction system can be measured in a variety of ways, including immunologic, chromatographic, electrophoretic, and the like.

Such β-secretase cleavage detection methods are particularly useful for screening test compounds to determine their ability to inhibit β-secretase mediated cleavage of APP. In such cases, a test compound is first identified by the methods described herein using invention peptides. Those test compounds that have the ability to inhibit the β-secretase-mediated cleavage of invention peptides are further tested for the ability to inhibit β-secretase-mediated cleavage of APP. The test compound is added to a reaction system where the substrate component is APP and the effect of the test compound on production of cleavage product is observed. Those compounds which inhibit the production of cleavage product(s) from APP are considered to be potential therapeutic agents for treatment of conditions associated with increased Aβ production such as Alzheimer's disease.

The reaction system will usually comprise β-secretase that will be either a purified or partially purified native β-secretase obtained from a cellular source. The cellular source may be a recombinant host cell that expresses β-secretase by virtue of having been transfected with an expression vector encoding β-secretase. Alternatively, β-secretase may be obtained from a cellular source that naturally (i.e., non-recombinantly) expresses β-secretase. Such a non-recombinant source could be a cell line having a sufficiently high level of expression of native β-secretase. The invention peptide substrate may include any one of the peptides exemplified in Table 2. The peptide substrate may be recombinant or synthetically derived. The reaction system can employ a wide variety of solid phase detection systems which permit observance of the production of β-secretase cleavage products over time or the disappearance of substrate over time. The methods will be particularly useful for determining the ability of test compounds to inhibit β-secretase mediated cleavage.

The assay may be performed by combining an at least partially purified β-secretase with at least one invention peptide substrate in the presence of the test substance. Conditions are maintained such that the β-secretase cleaves the invention peptide substrate into an amino-terminal fragment and a carboxy-terminal fragment in the absence of a substance which inhibits such cleavage. Cleavage of the peptide substrate in the presence of the test compound is compared with that in the absence of the test compound, and those test substances which provide significant inhibition of the cleavage activity (usually at least about 25% inhibition, more usually at least about 50% inhibition, preferably at least about 75% inhibition, and often at least about 90% inhibition or higher) are considered to be β-secretase inhibitors. Such β-secretase inhibitors may then be subjected to further in vitro and/or in vivo testing to determine if they inhibit the production of Aβ in cellular and animal models. As well, the cleavage products thus produced can be purified and used as immunogens to provide for antibodies specific for each of the "amino terminal" and "carboxy terminal" fragments, which, in turn, can be used to identify such fragments in other assays.

The screening assays of β-secretase and the invention peptide substrate are conveniently performed using "sandwich" assays where the amino-terminal or the carboxy-terminal fragment produced by cleavage is captured on a solid phase. The captured fragment may then be detected using an antibody specific for the end of the fragment exposed by β-secretase cleavage. An exemplary antibody is an antibody raised against any cleavage products produced as a result of β-secretase activity. The binding of the antibody to the cleaved cleavage product is detected using conventional labeling systems, such as horseradish peroxidase or other detectable enzyme labels, which are bound to the antibody directly (covalently), or indirectly through intermediate linking substances, such as biotin and avidin.

The compounds selected above may also be used to inhibit cleavage of native or recombinant APP by β-secretase in an in vitro assay. Compounds selected by the in vitro system, may in turn, be used as listed below.

Pharmaceutical Compositions and Therapeutic Methods

The present invention further comprises methods for inhibiting the β-secretase mediated cleavage of APP to APP cleavage products in cells, where the method comprises administering to the cells compounds selected by the method described herein. The compounds may be added to cell culture in order to inhibit APP cleavage which results in Aβ production. The compounds may also be administered to a patient in order to inhibit β-secretase mediated APP cleavage which results in pathogenic Aβ production and the deposition of amyloid β-plaque associated with Alzheimer's Disease and other Aβ-related conditions.

The present invention further comprises pharmaceutical compositions incorporating a compound selected by the herein-described methods and including a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosures of which are incorporated herein by reference.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The concentration of the compound in the pharmaceutical carrier may vary widely, i.e., from less than about 0.1% by weight of the pharmaceutical composition to about 20% by weight, or greater. Typical pharmaceutical composition for intramuscular injection would be made up to contain, for example, one to four ml of sterile buffered water and one gg to one mg of a compound identified by the methods of the present invention. A typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of Aβ, such as Alzheimer's disease, Down's syndrome, and advanced aging of the brain. In therapeutic applications, the pharmaceutical compositions are administered to a subject in need thereof already suffering from the disease. The pharmaceutical compositions will be administered in an amount sufficient to inhibit further deposition of Aβ plaque. An amount adequate to accomplish this is a "therapeutically effective dose." Such a therapeutically effective dose will depend on the extent of the disease, the size of the host, and the like, but will generally range from about 1 μg to 100 mg of the compound per kilogram of body weight of the host, with dosages of 10 μg to 1 mg/kg being more commonly employed.

For prophylactic applications, the pharmaceutical compositions of the present invention are administered to a host susceptible to the Aβ-related disease, but not already suffering from such disease. Such hosts may be identified by genetic screening and clinical analysis, as described in the medical literature (e.g. Goate, 1991, Nature 349:704–706). The pharmaceutical compositions will be able to inhibit or prevent deposition of the Aβ plaque at a symptomatically early stage, preferably preventing even the initial stages of the β-amyloid disease. The amount of the compound required for such prophylactic treatment, referred to as a prophylactically-effective dosage, is generally the same as described above for therapeutic treatment.

β-Secretase Substrates

The β-secretase substrates of the invention resemble the corresponding sequences from the Swedish mutation with specific amino acid substitutions incorporated therein. The sequence from the Swedish mutation corresponding to the peptides of the present invention is shown in SEQ ID NO: 257. The Swedish mutation results from a double substitution of $ASN_{595}$-$LEU_{596}$ for the $LYS_{595}$-$MET_{596}$ which are present in the wild type 695 isoform of APP.

The invention peptides are characterized as not only containing β-secretase cleavage sites but also are hydrolyzed faster than the Swedis sequence, SEQ ID NO: 257. The herein disclosed invention peptides can themselves provide substrates containing a β-secretase cleavage site and can serve as well as a starting point for creating derivative peptides. A distinguishing feature of the invention peptides is that data disclosed herein show that some of the invention peptides are hydrolyzed at least 33 times faster than the Swedish mutant APP sequence of SEQ ID NO: 257.

Based on the disclosure provided herein β-secretase substrates can be produced using standard biochemical synthesis and recombinant nucleic acid techniques. Techniques for chemical synthesis of peptides are well known in the art. (See, for example, Vincent, in *Peptide and Protein Drug Delivery*, New York, N.Y., Dekker, 1990).

Recombinant synthesis techniques for peptides are also well known in the art. Such techniques employ a nucleic acid template for peptide synthesis. Starting with a particular amino acid sequence and the known degeneracy of the genetic code, a large number of different encoding nucleic acid sequences can be obtained. The degeneracy of the genetic code arises because almost all amino acids are encoded for by different combinations of nucleotide triplets or "codons". The translation of a particular codon into a particular amino acid is well known in the art (see, e.g., lewin *GENES IV*, p. 119, Oxford University Press, 1990).

Amino acids are encoded for by codons as follows:
A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA,L CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUW
W=Trp=Tryptophan: codon UGG
Y=Tyr=Tyrosine: codons UAC, UAU Recombinant synthesis of peptides is achieved in a host cell using an expression vector. An expression vector contains recombinant nucleic acid encoding a desired peptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Generally, the regulatory elements that are present in an expression vector include a transcriptional promoter, a ribosome binding site, a terminator, and an optionally present operator. A preferred element is a polyadenylation signal providing for processing in eukaryotic cells. Other preferred elements include an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Nucleic acid encoding a peptide can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Techniques for introducing nucleic acid into an appropriate environment for expression, for expressing the nucleic acid to produce protein, and for isolating expressed proteins are will known in the art. Examples of such techniques are provided in references such as Ausubel, *Current Protocols in Molecular Biology*, John Wiley, 1987–1998, and Sambrook et al., in *Molecular Cloning, A Laboratory Manual*, 2nd Edition, Cold Spring Harbor Laboratory Press, 1989.

Examples are provided below to further illustrate different features and advantages of the present invention. The examples also illustrate useful methodology for practicing the invention. These examples do not limit the claimed invention.

EXAMPLE 1

Synthesis of β-secretase peptide substrates of the invention

The present inventors have established the preferred substrate amino acid sequence for β-secretase, an enzyme relevant to Alzheimer's Disease, through the utilization of synthetic combinatorial peptide libraries based on the core structure of amyloid precursor protein (APP) at the natural site of cleavage by β-secretase. A set of 8 synthetic peptide libraries was generated such that each library included one amino acid position along the APP polypeptide chain that was varied to include each component of a set of amino acids.

These libraries were developed on an eight residue core structure of APP that covered the known cleavage site of β-secretase, as shown in FIG. 1, where X is a set of all amino acids, with the exception of Met and Cys. In each case, the library was represented by an amino acid sequence where seven of the eight residue positions were identical with the corresponding residues in Swedish mutant APP and the eighth residue, indicated by X, was varied through the set of amino acids, resulting in a library of sequences. Thus, eight such libraries were developed by placing the site of variation at each position along the APP amino acid sequence. These libraries, as well as individual peptide substrates, were obtained commercially or synthesized using a standard peptide synthesis double-coupling protocol from Applied Biosystems Incorporated (AB) and an AB peptide synthesizer (Foster City, Calif.) model 430A. To produce a library of peptide sequences, one equivalent of an equimolar mixture of a set of Boc-protected amino acids was substituted in place of the residue normally found at the respective position in Swedish mutant APP. Consequently, 8 such libraries were generated by inserting the site of amino acid mixture incorporation at each point along the APP peptide chain from P4 to P4' as illustrated in FIG. 1. A general report of the method of peptide library synthesis and characterization can be found elsewhere. See Ramjit, H. G.; Kruppa, G. H.; Spier, J. P.; Ross, III, C. W.; Garsky, V. M. "The significance of monoisotopic and carbon-13 isobars for the identification of a 19-component dodecapeptide library by positive ion electrospray Fourier transform ion cyclotron resonance mass spectrometry", *Rapid Commun. Mass Spectrom.* 2000, 14, 1368–1376, which is incorporated by reference in its entirety.

EXAMPLE 2

Determination of β-secretase Activity

Following synthesis and purification, each of the eight peptide libraries was incubated with the enzyme β-secretase and the relative rates of cleavage of each individual peptide library component was followed with liquid chromatography/mass spectrometry (LC/MS) with analysis of both the depletion of the full length peptide substrate, as well as the formation of peptide cleavage fragments. The enzyme β-secretase was incubated at concentrations ranging from 5 to 50 nM at pH 4.5 with each of the peptide libraries and/or mixtures of synthetic peptide substrates.

For all incubations, the concentration of each individual peptide substrate was held at 1 µM to avoid precipitation, which could be observed at higher substrate concentrations with some of the more insoluble substrates. The mixtures of substrates and enzyme were incubated in an Agilent Technology 1100 series liquid chromatograph with a temperature controlled autosampler. The temperature for all β-secretase enzymatic assays was held constant at 37° C. A 100 µl aliquot of each reaction mixture was injected onto a 1×50 mm C18 reverse phase 1c column (Metachem Technologies Inc., Torrance, Calif.) every two hours to monitor reaction progress. After injection, a highly optimized solvent gradient was delivered to the column to maximize resolving power for each of the substrate library components. Optimal performance was obtained with a gradient starting at 20% solvent B (B=Acetonitrile with 0.05% trifluoroacetic acid, A=0.05% TFA in H2O) and increasing to 40% solvent B over 40 minutes. After the LC/MS run, the data were processed by selected-ion chromatograms for each of the peptide substrate library components by extracting 0.5 Da mass windows surrounding the calculated mass values of each of the peptides.

Extracting these data at each reaction time allowed the relative depletion of each substrate to be followed. For example, FIG. 2 illustrates the differences in rates of cleavage observed for all peptide library components from the P1' peptide library when treated with the enzyme β-secretase. Some peptide library components were observed to react and the corresponding peak areas decreased with time, while the peak areas of those that were not processed by β-secretase remained fairly constant. Those components that were shown to deplete the most readily were considered to be preferred residues at the site of variation. For clarity, only the P1' library components that were most rapidly hydrolyzed by β-secretase (P1'=Glu and P1'=Ala), one intermediate sequence (P1'=Asp—the residue normally present in Swedish mutant APP), and two peptides that were not cleaved by β-secretase (P1'=Gly and P1'=Pro) are shown in FIG. 2. The data predicted that either Glu or Ala in position P1' would be superior substrates for the enzyme β-secretase.

Figure 3:
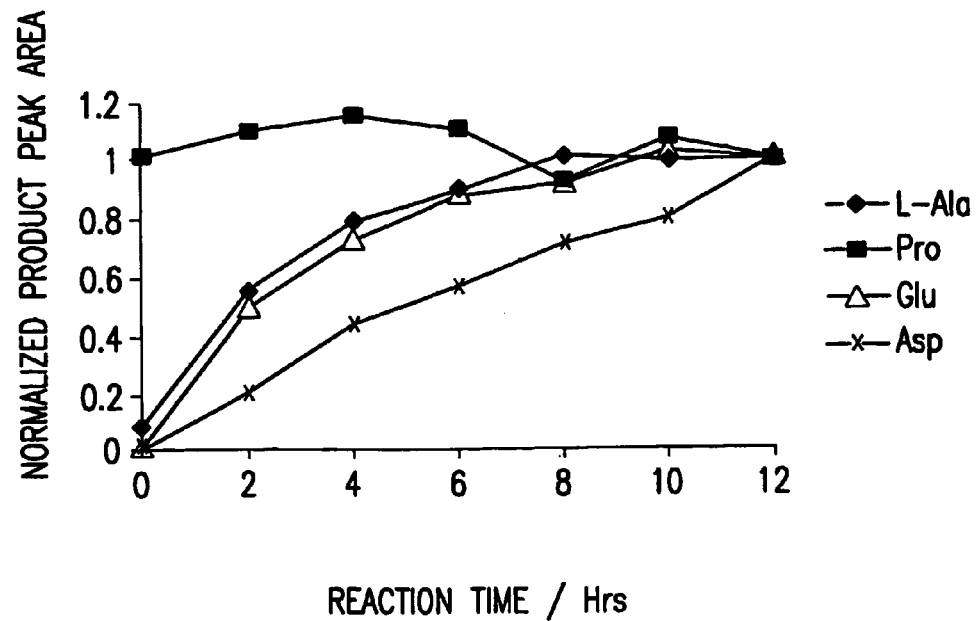
FIG. 3 illustrates the relative preference of β-secretase for a specified amino acid based upon an analysis of a cleavage product (C-terminal fragment) formed after cleavage of the invention peptide substrate(s) derived from the P1' peptide library by the β-secretase.

A similar relative preference for P1'=Glu or Ala was deduced from the analysis of the formation of cleavage products, that is, by the detection of peptide cleavage products representing the C-terminal fragments from the P1' peptide library as shown in FIG. 3. In this case, the preferred residue leads to more rapid formation of hydrolyzed product as shown by the more rapid and comparable rates of formation of the products represented by P1'=Ala and P1'=Glu. Again, the P1'=Asp product shows formation consistent with this residue being less conducive to β-secretase hydrolysis than either Glu or Ala. Thus, the preferred residues for the P1' substrate site were predicted to be Glu and Ala, based on the P1' peptide library analysis.

Figure 4:
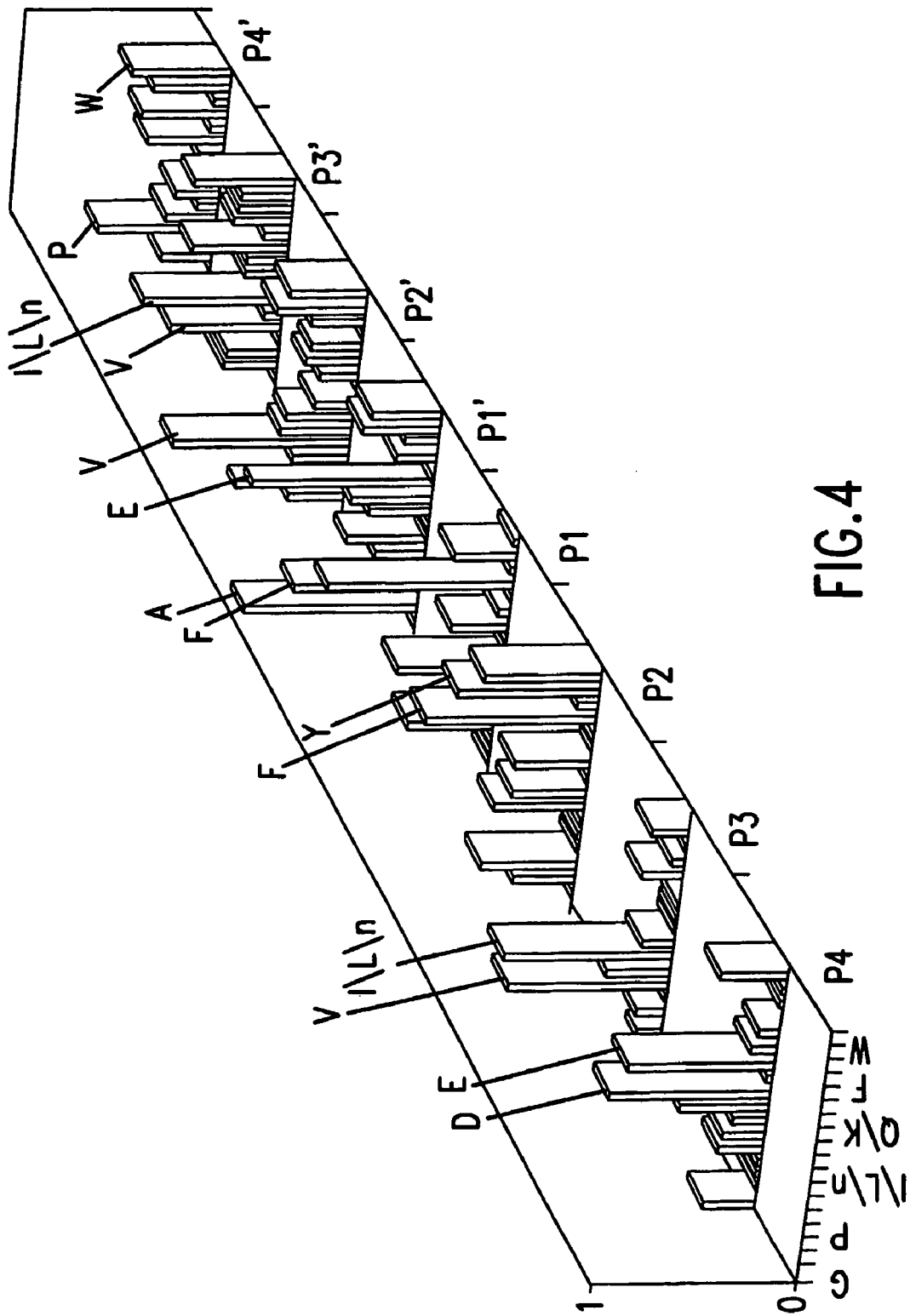
FIG. 4 depicts a graph showing the most preferred residues for a peptide substrate sequence based upon the rate of hydrolysis of a substrate by β-secretase. The data show the preferred sequence at specific positions of an 8-mer sequence that increases the rate of hydrolysis of the substrate sequence by β-secretase.

A similar detailed analysis was carried out with each of the 8 peptide libraries from P4 to P4' and graph summarizing the results of all peptide library work is shown in FIG. 4. In this figure, the relative preference for each amino acid surveyed is represented by the height of the bars at each position along the peptide chain from P4 to P4'.

TABLE 1

|  | P4 | P3 | P2 | P1 | P1' | P2' | P3' | P4' |
|---|---|---|---|---|---|---|---|---|
| APP: | E | V | N | L | D | A | E | P |
| Preferred | D = E | L\I\n | F | F | A = E | V | V = I/L/n | P |
| 2nd | I\L\n | V | Y | I\L\n | S | I\L\n | E | W |
| 3rd | V | N | E | Y | I\L\n | A | Y | F |

As shown in Table 1 above, the residues normally found in at each position along the sequence of the Swedish version of APP were only infrequently identified by this approach to be the most preferred, or even the second most preferred residue. The data allow the compilation of residues to generate substrate sequences that are preferred by β-secretase, or processed much more rapidly than even the Swedish mutant sequence of APP. These findings have been validated by designing and synthesizing specific amino sequences incorporating the preferred amino acids for residues at P1, P1' and P2'.

Figure 5:
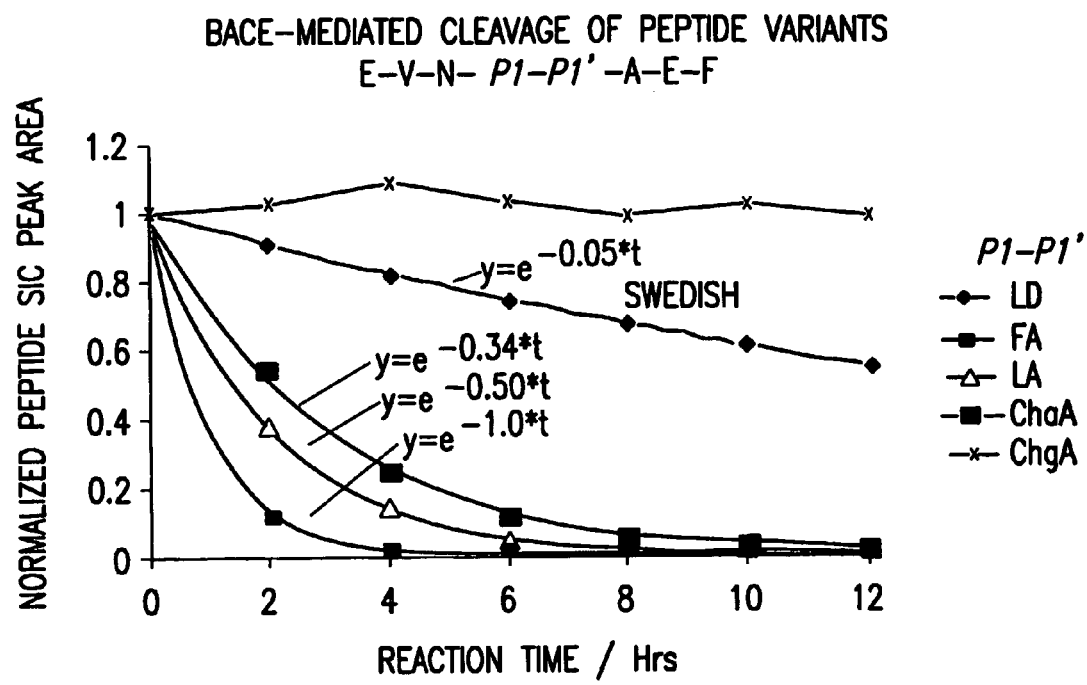
FIG. 5 depicts the increase in the rate of hydrolysis of synthetic 8-mer peptide substrates observed with the incorporation of amino acid substitutions for positions P1 and P1' based on the preference for amino acids Phe and Ala, respectively. The replacement of Ala for Asp 597 in an 8-mer peptide sequence corresponding to the Swedish mutant sequence 695 resulted in an increase in the observed rate of hydrolysis of 10 relative to the Swedish mutant sequence. Additional incorporation of Phe for Leu 596 in an 8-mer peptide sequence resulted in an observed hydrolysis by β-secretase that was 17 times higher than that observed with the Swedish mutant sequence.

This new substrate sequence was shown to be hydrolyzed by β-secretase at least 30 times faster than the Swedish mutant APP sequence. For example, FIG. 5 shows the results obtained with individual, pure peptides obtained with sequence information derived from the peptide library study. Five peptide sequences were incubated simultaneously in the presence of β-secretase to determine if incorporation of the library results would result in a superior substrate. This study was done to ascertain if incorporation of the residues that were found to be preferred from the peptide library studies would result in a substrate that is hydrolyzed faster than the normal Swedish mutant APP sequence. Five individual peptide sequences were incubated simultaneously with β-secretase, analogous to the peptide library experiments.

The peptide sequences used in these experiments were:

```
EVNLDAEF         (SEQ ID NO: 257)

EVNLAAEF         (SEQ ID NO: 258)
```

-continued

| | |
|---|---|
| EVNFAAEF | (SEQ ID NO: 259) |
| EVNChgAAEF | (SEQ ID NO: 263) |
| EVNChaAAEF | (SEQ ID NO: 264) | where Chg and Cha are cyclohexylglycine and cyclohexylalanine residues, respectively. The non-natural Chg and Cha were included to determine if variations on the aromatic ring of F, found to be preferred for P1, would result in even faster β-secretase-mediated hydrolysis. As is shown in FIG. 5, the single point mutation of the aspartic acid in position P1' to Ala resulted in a substrate that was hydrolyzed by β-secretase 10 times faster than the corresponding Swedish mutant sequence. Additionally, inclusion of the predicted phenylalanine residue in position P1 in conjunction with the Ala substitution at P1' resulted in an additional factor of almost 2 increase in the observed rate of hydrolysis with β-secretase. This resulted in a substrate that was hydrolyzed roughly 17 times faster than the Swedish mutant sequence. Additional substitutions that have been incorporated include the valine residue at P2' for a substrate that has the sequence FAV at position P1-P1'-P2'. This FAV-containing peptide was found be hydrolyzed by β-secretase roughly 30 times faster than the Swedish mutant APP sequence. These results validate the approach involving the establishment of a preferred substrate sequence by combination of single point library study results. Incorporation of additional residues to establish even better is made possible by the present data. Table 2 discloses 256 sequences predicted to be good β-secretase substrates from the selection of the two most preferred residues at each position through the 8-mer sequence.

TABLE 2

| SEQUENCE | SEQUENCE ID | SEQUENCE | SEQUENCE ID |
|---|---|---|---|
| EIYLEVIW | 1 | EIYFEVVW | 2 |
| DIYLEVIW | 3 | DIYFEVVW | 4 |
| EVYLEVIW | 5 | EVYFEVVW | 6 |
| DVYLEVIW | 7 | DVFFEAIP | 8 |
| 2EIFLEVIW | 9 | EIYLAAIP | 10 |
| DIFLEVIW | 11 | DIYLAAIP | 12 |
| EVFLEVIW | 13 | EVYLAAIP | 14 |
| DVFLEVIW | 15 | DVYLAAIP | 16 |
| EIYFEVIW | 17 | EIFLAAIP | 18 |
| DIYFEVIW | 19 | DIFLAAIP | 20 |
| EVYFEVIW | 21 | EVFLAAIP | 22 |
| DVYFEVIW | 23 | DVFLAAIP | 24 |
| EIFFEVIW | 25 | EIYFAAIP | 26 |
| DIFFEVIW | 27 | DIYFAAIP | 28 |
| EVFFEVIW | 29 | EVYFAAIP | 30 |
| DVFFEVIW | 31 | DVYFAAIP | 32 |
| EIYLAVIW | 33 | EIFFAAIP | 34 |

TABLE 2-continued

| SEQUENCE | SEQUENCE ID | SEQUENCE | SEQUENCE ID |
|---|---|---|---|
| DIYLAVIW | 35 | DIFFAAIP | 36 |
| EVYLAVIW | 37 | EVFFAAIP | 38 |
| DVYLAVIW | 39 | DVFFAAIP | 40 |
| EIFLAVIW | 41 | EIYLEVVP | 42 |
| DIFLAVIW | 43 | DIYLEVVP | 44 |
| EVFLAVIW | 45 | EVYLEVVP | 46 |
| DVFLAVIW | 47 | DVYLEVVP | 48 |
| EIYFAVIW | 49 | EIFLEVVP | 50 |
| DIFFAAVW | 51 | DIFLEVVP | 52 |
| EVFFAAVW | 53 | EVFLEVVP | 54 |
| DVFFAAVW | 55 | DVFLEVVP | 56 |
| EIYLEVIP | 57 | DVYFEVVW | 58 |
| DIYLEVIP | 59 | EIFFEVVW | 60 |
| EVYLEVIP | 61 | DIFFEVVW | 62 |
| DVYLEVIP | 63 | EVFFEVVW | 64 |
| EIFLEVIP | 65 | DVFFEVVW | 66 |
| DIFLEVIP | 67 | EIYLAVVW | 68 |
| EVFLEVIP | 69 | DIYLAVVW | 70 |
| DVFLEVIP | 71 | EVYLAVVW | 72 |
| EIYFEVIP | 73 | DVYLAVVW | 74 |
| DIYFEVIP | 75 | EIFLAVVW | 76 |
| EVYFEVIP | 77 | DIFLAVVW | 78 |
| DVYFEVIP | 79 | EVFLAVVW | 80 |
| EIFFEVIP | 81 | DVFLAVVW | 82 |
| DIFFEVIP | 83 | EIYFAVVW | 84 |
| EVFFEVIP | 85 | DIYFAVVW | 86 |
| DVFFEVIP | 87 | EVYFAVVW | 88 |
| EIYLAVIP | 89 | DVYFAVVW | 90 |
| DIYLAVIP | 91 | EIFFAVVW | 92 |
| EVYLAVIP | 93 | DIFFAVVW | 94 |
| DVYLAVIP | 95 | EVFFAVVW | 96 |
| EIFLAVIP | 97 | DVFFAVVW | 98 |
| DIFLAVIP | 99 | EIYLEAVW | 100 |
| EVYFAAVP | 101 | DIYLEAVW | 102 |
| DVYFAAVP | 103 | EVYLEAVW | 104 |
| EIFFAAVP | 105 | DVYLEAVW | 106 |
| DIFFAAVP | 107 | EIYFEVVP | 108 |
| EVFFAAVP | 109 | DIYFEVVP | 110 |

TABLE 2-continued

| SEQUENCE | SEQUENCE ID | SEQUENCE | SEQUENCE ID |
|---|---|---|---|
| DVFFAAVP | 111 | EVYFEVVP | 112 |
| DIYFAVIW | 113 | DVYFEVVP | 114 |
| EVYFAVIW | 115 | EIFFEVVP | 116 |
| DVYFAVIW | 117 | DIFFEVVP | 118 |
| EIFFAVIW | 119 | EVFFEVVP | 120 |
| DIFFAVIW | 121 | DVFFEVVP | 122 |
| EVFFAVIW | 123 | EIYLAVVP | 124 |
| DVFFAVIW | 125 | DIYLAVVP | 126 |
| EIYLEAIW | 127 | EVYLAVVP | 128 |
| DIYLEAIW | 129 | DVYLAVVP | 130 |
| EVYLEAIW | 131 | EIFLAVVP | 132 |
| DVYLEAIW | 133 | DIFLAVVP | 134 |
| EIFLEAIW | 135 | EVFLAVVP | 136 |
| DIFLEAIW | 137 | DVFLAVVP | 138 |
| EVFLEAIW | 139 | EIYFAVVP | 140 |
| DVFLEAIW | 141 | DIYFAVVP | 142 |
| EIYFEAIW | 143 | EVYFAVVP | 144 |
| DIYFEAIW | 145 | DVYFAVVP | 146 |
| EVYFEAIW | 147 | EIFFAVVP | 148 |
| DVYFEAIW | 149 | DIFFAVVP | 150 |
| EIFFEAIW | 151 | EVFFAVVP | 152 |
| DIFFEAIW | 153 | DVFFAVVP | 154 |
| EVFFEAIW | 155 | EIYLEAVP | 156 |
| DVFFEAIW | 157 | EIFLEAVW | 158 |
| EIYLAAIW | 159 | DIFLEAVW | 160 |
| DIYLAAIW | 161 | EVFLEAVW | 162 |
| EVELAVIP | 163 | DVFLEAVW | 164 |
| DVFLAVIP | 165 | EIYFEAVW | 166 |
| EIYFAVIP | 167 | DIYFEAVW | 168 |
| DIYFAVIP | 169 | EVYFEAVW | 170 |
| EVYFAVIP | 171 | DVYFEAVW | 172 |
| DVYFAVIP | 173 | EIFFEAVW | 174 |
| EIFFAVIP | 175 | DIFFEAVW | 176 |
| DIFFAVIP | 177 | EVFFEAVW | 178 |
| EVFFAVIP | 179 | DVFFEAVW | 180 |
| DVFFAVIP | 181 | EIYLAAVW | 182 |
| EIYLEAIP | 183 | DLYLAAVW | 184 |
| DIYLEAIP | 185 | EVYLAAVW | 186 |
| EVYLEAIP | 187 | DVYLAAVW | 188 |
| DVYLEAIP | 189 | EIFLAAVW | 190 |
| EIFLEAIP | 191 | DIFLAAVW | 192 |
| DIFLEAIP | 193 | EVFLAAVW | 194 |
| EVFLEAIP | 195 | DVFLAAVW | 196 |
| DVFLEAIP | 197 | EIYFAAVW | 198 |
| EIYFEAIP | 199 | DIYFAAVW | 200 |
| DIYFEAIP | 201 | EVYFAAVW | 202 |
| EVYFEAIP | 203 | DVYFAAVW | 204 |
| DVYFEAIP | 205 | EIFFAAVW | 206 |
| EIFFEAIP | 207 | DIYLEAVP | 208 |
| DIFFEAIP | 209 | EVYLEAVP | 210 |
| EVFFEAIP | 211 | DVYLEAVP | 212 |
| EVYLAAIW | 213 | EIFLEAVP | 214 |
| DVYLAAIW | 215 | DIFLEAVP | 216 |
| EIFLAAIW | 217 | EVFLEAVP | 218 |
| DIFLAAIW | 219 | DVFLEAVP | 220 |
| EVFLAAIW | 221 | EIYFEAVP | 222 |
| DVFLAAIW | 223 | DIYFEAVP | 224 |
| EIYFAAIW | 225 | EVYFEAVP | 226 |
| DIYFAAIW | 227 | DVYFEAVP | 228 |
| EVYFAAIW | 229 | EIFFEAVP | 230 |
| DVYFAAIW | 231 | DIFFEAVP | 232 |
| EIFFAAIW | 233 | EVFFEAVP | 234 |
| DIFFAAIW | 235 | DVFFEAVP | 236 |
| EVFFAAIW | 237 | EIYLAAVP | 238 |
| DVFFAAIW | 239 | DIYLAAVP | 240 |
| EIYLEVVW | 241 | EVYLAAVP | 242 |
| DIYLEVVW | 243 | DVYLAAVP | 244 |
| EVYLEVVW | 245 | EIFLAAVP | 246 |
| DVYLEVVW | 247 | DIFLAAVP | 248 |
| EIFLEVVW | 249 | EVFLAAVP | 250 |
| DIFLEVVW | 251 | DVFLAAVP | 252 |
| EVFLEVVW | 253 | EIYFAAVP | 254 |
| DVFLEVVW | 255 | DIYFAAVP | 256 |

EXAMPLE 3

Additional Assays

The β-secretase peptide substrates can be employed in assays measuring production of cleavage products. Cleavage of β-secretase substrates can be measured by detecting formation of the N- or C-terminal cleavage products of any of the herein disclosed peptide substrates. The presence of either of these products can be measured using techniques such as those employing antibodies and radioactive, electrochemiluminescent or fluorescent labels. If needed or desirable, a purification step enriching the different products may be employed. Examples of purification steps include the use of antibodies, separation gels, and columns.

EXAMPLE 4

Cleavage Product Detection

The cleavage products of the herein disclosed peptide substrates may be detected using a sandwich assay employing an antibody to capture the cleavage peptide and an antibody to detect the presence of the cleavage peptide. Detection may be achieved by using electrochemiluminescence (ECL) (Yang et al., 1994, Bio/Technology 12:193–194; Khorkova et al., 1998. Journal of Neuroscience Methods 82:159–166), and an Origen 1.5 Analyzer (Igen Inc., Gaithersburg, Md.).

EXAMPLE 5

Inhibition Studies

Inhibition studies can be performed to demonstrate that the β-secretase activity is catalyzed by a bona fide APP processing enzyme in cells and is not simply due to a spurious proteolytic activity. The studies may examine the effects of various peptide substrates from Table 2 on cleavage at the β-secretase scissile bond of the substrates in an in vitro assays using any known inhibitor of β-secretase.

The effect of a β-secretase inhibitor on β-secretase activity may, for example, be measured using Chinese hamster ovary fibroblasts (CHO cells) that stably express any one of the peptide substrates of the invention. CHO cells expressing the invention peptides are grown in a suitable medium under appropriate growth conditions, exemplified by 90% DMEM, 10% fetal bovine serum, 2 mM glutamine, 100 μg/ml each of penicillin and streptomycin, and 0.2 mg/ml G418. The cells are seeded in 96-well dishes at 2×10⁴ cells/well. Cleavage product formation may be detected using radiolabeled antibodies specific for at least one cleavage product of the reference peptide substrate that is used to transfect the CHO cells.

Treatment of CHO cells expressing the invention peptides with a known β-secretase inhibitor is expected to block cleavage products from being secreted from such cells in a dose-dependent manner with $IC_{50}$ values for suppression of such products that are similar to values reported in the literature.

Similarly, a β-secretase inhibitor is expected to inhibit "solubilized β-secretase" mediated processing of any of the invention peptide substrate sequences shown in Table 1 that eventually result in the generation of the cleavage related products.

EXAMPLE 6

Figure 6:
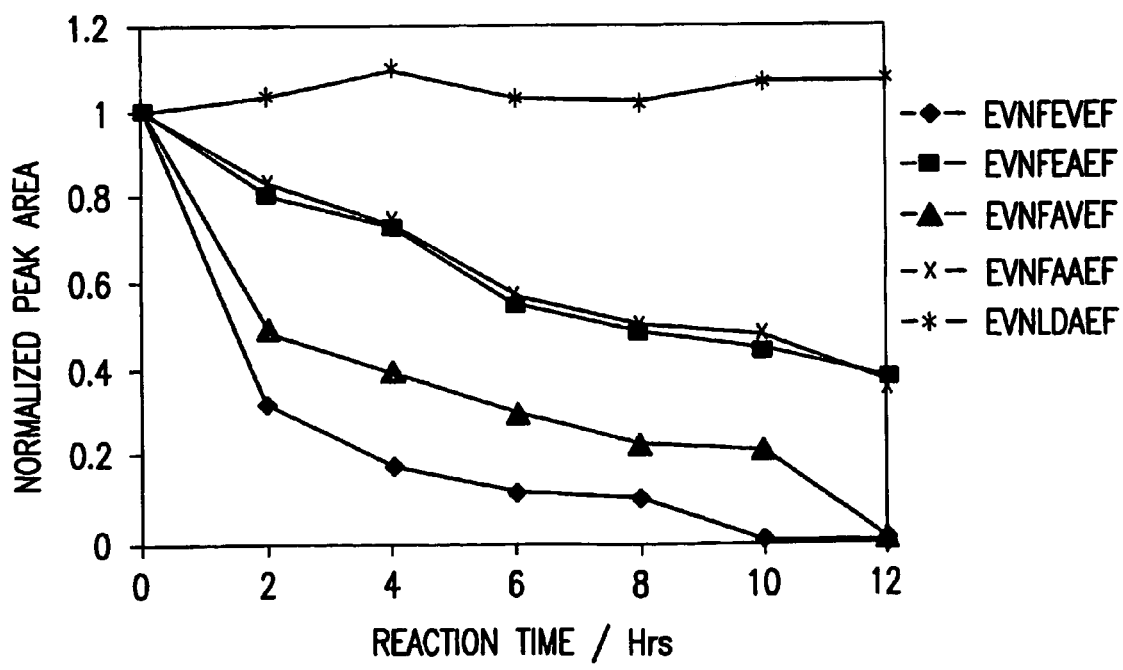
FIG. 6 shows the rate of hydrolysis for the Swedish mutant (EVNLDAEF; SEQ ID NO: 257) compared with the rate for the invention peptides EVNFAAEF (SEQ ID NO: 259); EVNFEAEF (SEQ ID NO: 260); EVNFAVEF (SEQ ID NO: 261); and EVNFEVEF (SEQ ID NO: 262).

A Preferred Substrate that is Hydrolyzed 60 Times Faster than the Swedish Mutant FIG. 6 shows the rate of hydrolysis observed for the Swedish mutant (SEQ ID NO: 257) and four of the invention peptides. One invention peptide in particular, EVNFEVEF (SEQ ID NO: 262), was found to be an especially good substrate for β-secretase, with its rate of hydrolysis being 60 times faster than the rate of hydrolysis for SEQ ID NO: 257. Table 3 shows these results plus results for EVNLAAEF (SEQ ID NO: 258).

TABLE 3

|  |  | Relative rates of hydrolysis |
|---|---|---|
| EVNLDAEF | (SEQ ID NO: 257) | 1 |
| EVNLAAEF | (SEQ ID NO: 258) | 10 |
| EVNFAAEF | (SEQ ID NO: 259) | 17 |
| EVNFEAEF | (SEQ ID NO: 260) | 17 |
| EVNFAVEF | (SEQ ID NO: 261) | 30 |
| EVNFEVEF | (SEQ ID NO: 262) | 60 |

Other embodiments are within the following claims. While several embodiments have been shown and described, various modifications may be made without departing from the spirit and scope of the present invention.

What is claimed:

1. A method for assaying for increased β-secretase activity comprising measuring a cleavage product produced from cleavage by β-secretase of an APP substrate comprising a β-secretase peptide substrate comprising a β-secretase cleavage site and having the formula P4-P3-P2-P1-P1'-P2'-P3'-P4', where P4 is selected from the group consisting of D, E, I, L and V;
P3 is selected from the group consisting of L, I, V and N;
P2 is selected from the group consisting of F, Y, E and N;
P1 is selected from the group consisting of F, I, L and Y;
P1' is selected from the group consisting of A, E, S, I, L and D;
P2' is selected from the group consisting of V, I, L and A;
P3' is selected from the group consisting of V, I, L, E and Y; and
P4' is selected from the group consisting of P, W and F;
where P4-P3-P2-P1-P1'-P2'-P3'-P4' cannot simultaneously be chosen such that they comprise the Swedish mutation β-secreatse cleavage site (SEQ ID NO: 257); and where an increase in β-secretase activity is determined when the amount of the cleavage product is increased relative to the amount of the cleavage product produced from an APP substrate having the Swedish mutation at said β-secretase cleavage site (SEQ ID NO: 257).

2. The method of claim 1 wherein said β-secretase peptide substrate corresponds to positions 593–600 of APP695.

3. The method of claim 2 wherein said β-secretase peptide substrate comprises SEQ ID NO: 262.

4. The method of claim 1 wherein the β-secretase activity is measured using an antibody that binds to the amino terminus of the β-CTF cleavage product.

5. The method of claim 1 wherein the cleavage product detected is β-CTF.

* * * * *